(12) United States Patent
Nakagawa et al.

(10) Patent No.: US 10,209,236 B2
(45) Date of Patent: Feb. 19, 2019

(54) CELL ANALYZER SYSTEM, CELL ANALYZER PROGRAM, AND CELL ANALYZING METHOD

(71) Applicant: Sony Corporation, Tokyo (JP)

(72) Inventors: Kazuhiro Nakagawa, Saitama (JP); Shiori Oshima, Kanagawa (JP); Eriko Matsui, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/651,553

(22) PCT Filed: Nov. 12, 2013

(86) PCT No.: PCT/JP2013/006646
§ 371 (c)(1),
(2) Date: Oct. 13, 2015

(87) PCT Pub. No.: WO2014/103137
PCT Pub. Date: Jul. 3, 2014

(65) Prior Publication Data
US 2016/0041144 A1 Feb. 11, 2016

(30) Foreign Application Priority Data

Dec. 27, 2012 (JP) .................. 2012-285123

(51) Int. Cl.
*G06K 9/00* (2006.01)
*G01N 33/483* (2006.01)
(Continued)

(52) U.S. Cl.
CPC ........... *G01N 33/4833* (2013.01); *C12Q 1/02* (2013.01); *G01N 15/1468* (2013.01);
(Continued)

(58) Field of Classification Search
None
See application file for complete search history.

(56) References Cited

U.S. PATENT DOCUMENTS 7,246,012 B2* 7/2007 Kutsyy .............. G06K 9/00147
382/128
8,668,647 B2* 3/2014 Eskandari ............ A61B 5/0051
382/128
(Continued)

FOREIGN PATENT DOCUMENTS

JP 2003-527113 A 9/2003
JP 2004-008173 A 1/2004
(Continued)

OTHER PUBLICATIONS

Hayakawa et al., Intercellular network evaluation of the cardiac muscle cell. Regenerative Medicine. Feb. 1, 2011;10(Suppl):258.
(Continued)

*Primary Examiner* — Hadi Akhavannik
(74) *Attorney, Agent, or Firm* — Wolf, Greenfield & Sacks, P.C.

(57) ABSTRACT

A cell analyzer system according to the present technology includes an image acquisition unit, a vibration information extraction unit, and a vibration characteristics calculation unit. The image acquisition unit acquires a cell image by capturing cells at elapsed time. The vibration information extraction unit extracts vibration information attributable to spontaneous membrane potential vibration of cells from the cell image. The vibration characteristics calculation unit calculates vibration characteristics of the vibration information from the vibration information.

15 Claims, 27 Drawing Sheets

(51) Int. Cl.
*C12Q 1/02* (2006.01)
*G01N 15/14* (2006.01)
*G01N 33/50* (2006.01)
*G01N 15/10* (2006.01)

(52) U.S. Cl.
CPC . *G01N 33/5005* (2013.01); *G01N 2015/1006* (2013.01); *G01N 2015/1493* (2013.01)

(56) References Cited

U.S. PATENT DOCUMENTS

| | | | | |
|---|---|---|---|---|
| 8,712,139 | B2* | 4/2014 | Rittscher | G06K 9/0014 |
| | | | | 382/133 |
| 2006/0014137 | A1* | 1/2006 | Ghosh | G01N 21/6428 |
| | | | | 435/4 |
| 2006/0216688 | A1 | 9/2006 | Maher et al. | |
| 2006/0216689 | A1 | 9/2006 | Maher et al. | |
| 2006/0216690 | A1 | 9/2006 | Maher et al. | |
| 2007/0054266 | A1* | 3/2007 | Sato | G01N 33/5008 |
| | | | | 435/6.19 |
| 2007/0294778 | A1* | 12/2007 | Rich | A61K 49/0008 |
| | | | | 800/3 |
| 2008/0304732 | A1* | 12/2008 | Rittscher | A61B 5/1105 |
| | | | | 382/133 |
| 2009/0196482 | A1 | 8/2009 | Kobayashi et al. | |
| 2009/0202130 | A1 | 8/2009 | George et al. | |
| 2010/0209934 | A1* | 8/2010 | Oh | G01N 33/6872 |
| | | | | 435/6.16 |
| 2012/0149052 | A1* | 6/2012 | Grohovaz | G01N 33/5008 |
| | | | | 435/29 |
| 2013/0070971 | A1 | 3/2013 | Kunihiro et al. | |
| 2013/0224756 | A1* | 8/2013 | Cohen | C07K 14/195 |
| | | | | 435/6.17 |
| 2013/0321459 | A1 | 12/2013 | Hayakawa et al. | |
| 2013/0344559 | A1* | 12/2013 | Engeberg | C12N 13/00 |
| | | | | 435/173.1 |
| 2016/0041144 | A1* | 2/2016 | Nakagawa | C12Q 1/02 |
| | | | | 435/29 |
| 2016/0282338 | A1* | 9/2016 | Miklas | C12M 21/08 |
| 2016/0284081 | A1 | 9/2016 | Nakagawa et al. | |
| 2017/0069860 | A1* | 3/2017 | Zorlutuna | H01L 51/0575 |
| 2017/0246148 | A1* | 8/2017 | Kil | A61K 31/41 |

FOREIGN PATENT DOCUMENTS

| | | |
|---|---|---|
| JP | 2006-184207 A | 7/2006 |
| JP | 2006-525210 A | 11/2006 |
| JP | 2006-526389 A | 11/2006 |
| JP | 2006-329672 A | 12/2006 |
| JP | 2008-538287 A | 10/2008 |
| JP | 2009-118817 A | 6/2009 |
| JP | 2011-122953 A | 6/2011 |
| JP | 2011-174939 A | 9/2011 |
| JP | 2011-188860 A | 9/2011 |
| JP | 2012-014066 A | 1/2012 |
| WO | WO 2011/122200 A1 | 10/2011 |
| WO | WO 2011/132584 A1 | 10/2011 |

OTHER PUBLICATIONS

Kunihiro et al., Examination of the heartbeat evaluation technique of the cultured cardiac muscle cell by the animated image analysis. Regenerative Medicine. Feb. 1, 2011;10(Suppl):144.

Oshima et al., The three-dimensional information acquisition method of the viable cell using the Z-Stack animation image with the optical microscope. Bioimaging. Aug. 1, 2012;21(2):2010-211.

Uno et al., Development of new drug evaluation technique for the cardiac function by the animated image analysis. Japanese Association of Cardiovascular Pharmacology Koen Yoshishu. Dec. 2, 2012;21:47.

Oshima et al., Efficacy of motion analysis and visualization of neural cell for functional assessment, The Journal of Toxicological Sciences, Jun. 2013, vol. 38, No. Supplement, pS292.

Rossi et al., Super-resolution imaging of aquaporin-4 orthogonal arrays of particles in cell membranes, J of Cell Science 125(18), pp. 4405-4412.

Yamamura, Imaging analyses of ion channel molecule functions, Folia Pharmacologica Japonica, Aug. 9, 2013, vol. 142, No. 2, pp. 79-84.

Yamamura, Imaging analyses of ion channel molecule functions, Journal of Pharmacological Science, Mar. 15, 2013, vol. 121, No. Supplement 1, p. 10.

Betzig et al., Imaging Intracellular Fluorescent Proteins at Nanometer Resolution, Science, Sep. 15, 2006, vol. 313, pp. 1642-1645.

Crane et al., Determinants of aquaporin-4 assembly in orthogonal arrays revealed by live-cell single-molecule fluorescence imaging, Journal of Cell Science, 2009, vol. 122, No. 6, pp. 813-821.

Yamamura et al., New light on ion channel imaging by total internal reflection fluorescence (TIRF) microscopy, Journal of Pharmacological Sciences, 2015, vol. 128, pp. 1-7.

Japanese Office Action dated Jul. 25, 2017 in connection with Japanese Application No. 2014-554085 and English translation thereof.

Japanese Office Action dated Jul. 31, 2018 in connection with Japanese Application No. 2015-546279 and English translation thereof.

* cited by examiner (a)

(b)

(a)

(b)

(a)

(b)

(a)

(b)

CELL ANALYZER SYSTEM, CELL ANALYZER PROGRAM, AND CELL ANALYZING METHOD

CROSS REFERENCE TO RELATED APPLICATIONS

This is a U.S. National Stage Application under 35 U.S.C. § 371, based on International Application No. PCT/JP2013/006646, filed Nov. 12, 2013, which claims priority to Japanese Patent Application JP 2012-285123, filed Dec. 27, 2012, each of which is hereby incorporated by reference in its entirety.

TECHNICAL FIELD

The present technology relates to a cell analyzer system and a cell analyzing method for evaluating a status of a cell or a cell network.

BACKGROUND ART

Formation of iPS cells (see Patent Document 1) significantly progresses the fields including a regenerative medicine, tissue engineering and cell engineering. Evaluation of a cell status and evaluation of effects and impacts of a medicine on cells are highly demanded. Especially in neuron cells, a method of generating neuron cells from embryostem cells such as iPS cells has been established (see Patent Document 2). An effective way to evaluate neuron cells is sought.

An evaluation method of neuron cells often involves using an electrode array (see Patent Documents 3 to 5). The neuron cells function not as a cell simple substance, but as a circuit or a neural network. An evaluation method of the neural network involves locally applying electrical stimulation (see Patent Document 3), breaking a part of neurites and evaluating a recovery process (see Patent Document 4) or the like.

Patent Document 1: Japanese Patent Application Laid-open No. 2011-188860
Patent Document 2: Japanese Patent Application Laid-open No. 2006-525210
Patent Document 3: Japanese Patent Application Laid-open No. 2011-122953
Patent Document 4: Japanese Patent Application Laid-open No. 2009-118817
Patent Document 5: Japanese Patent Application Laid-open No. 2006-329672
Patent Document 6: Japanese Patent Application Laid-open No. 2004-008173

SUMMARY OF INVENTION

Problem to be Solved by the Invention

However, in the evaluation method of neuron cells using the electrode array as described in Patent Documents 3 to 5, a spatial range and resolution to be evaluated depend on the electrode array. Therefore, in order to evaluate neuron cells in a wide range at a high resolution, a large-sized and high-density electrode array has to be produced. In the evaluation method of neural network as described in Patent Documents 3 and 4, the network can be locally evaluated, but it is difficult to evaluate the neural network in a wide range.

In view of the circumstances as described above, an object of the present technology is to provide a cell analyzer system, a cell analyzing program and a cell analyzing method for effectively evaluating a cell and a cell network.

Means for Solving the Problem

In order to achieve the object, a cell analyzer system according to an embodiment of the present technology includes an image acquisition unit, a vibration information extraction unit, and a vibration characteristics calculation unit.

The image acquisition unit acquires a cell image by capturing cells at elapsed time.

The vibration information extraction unit extracts vibration information attributable to spontaneous membrane potential vibration of cells from the cell image.

The vibration characteristics calculation unit calculates vibration characteristics of the vibration information from the vibration information.

Spontaneous membrane potential vibration of cells and potential vibration in a cell group attributable to the spontaneous membrane potential vibration are affected by a status of the cells (such as vitality of the cells, expressions and functions of channels, a status of stimulation inputted to the cells, and a cell network formation status). Accordingly, vibration characteristics of vibration information (such as light intensity vibration as described later) attributable to the spontaneous membrane potential vibration reflect the status of the cells. The cell analyzer system can provide a user with the vibration characteristics. The user can evaluate the cell status based on the vibration characteristics.

The cell analyzer system may further include a range designation unit configured to designate an extraction range in the cell image, and the vibration information extraction unit may extract the vibration information from the extraction range.

By this configuration, the extraction range for extracting the vibration information in the cell image, and an image range including the cells and the cell group can be the extraction range. The range designation unit may designate the extraction range by a user's manipulated input, or may designate the extraction range by detecting the cells and the cell group with image processing.

The cell analyzer system may further includes an evaluation unit configured to evaluate one cell or a plurality of cells included in the extraction range based on the vibration characteristics.

As described above, the vibration characteristics reflect the status of the cells included in the extraction range designated by the range designation unit. Thus, the evaluation unit can evaluate the status of the cells based on the vibration characteristics (frequency, amplitude, vibration power etc.) of the vibration information.

The range designation unit may designate a range including one cell in the cell image as the extraction range, and the evaluation unit may evaluate a type and a strength of stimulation inputted to the cell.

The spontaneous membrane potential vibration of the cells is affected by stimulation inputted to the cells (such as exciting or inhibitory stimulation). Thus, the evaluation unit can evaluate a type or a kind of the stimulation inputted to the cells based on the vibration characteristics of the vibration information extracted from the extraction range including one cell.

The range designation unit may designate a range including a cell group including a plurality of cells as the extraction range in the cell image, and the evaluation unit may evaluate a cell network formation status in the cell group.

The vibration information extracted from the cell group is affected by the network formation status of the cells in the cell group. Thus, the evaluation unit can evaluate the network formation status of the cell group based on the vibration characteristics of the vibration information extracted from the extraction range including the cell group.

The vibration information extraction unit may extract intensity vibration of an electromagnetic wave as the vibration information.

The intensity vibration of electromagnetic waves (such as light and radiation) emitted from a substance fed to the cells (such as a fluorescent substance) and the cells themselves is affected by the spontaneous membrane potential vibration. Thus, it is possible to evaluate the cell status based on the vibration characteristics of the intensity vibration of light extracted from the cell image.

The vibration information extraction unit may extract motion vibration as the vibration information.

A cell and an intracellular motion vibration that can be extracted by an image motion analysis is affected by the spontaneous membrane potential vibration. Thus, it is possible to evaluate the cell status based on the vibration characteristics of the motion vibration extracted from the cell image.

The vibration characteristics calculation unit may apply frequency to the vibration information to calculate the vibration characteristics.

By applying a frequency analysis such as a fast Fourier transformation and a wavelet transformation to the vibration information, the vibration characteristics such as a frequency, an amplitude and vibration power of the vibration information can be calculated, which can be used to evaluate the cell status.

The vibration information extraction unit may extract a plurality types of vibration information from the extraction range.

By extracting a plurality types of vibration information (for example, light intensity vibration and motion vibration) from the same extraction range and comparing the similarity therebetween, an effect of the spontaneous membrane potential vibration on a variety of vibration information can be judged, which can be used to evaluate the cell status.

The range designation unit designates a range including a cell group in the cell image and a range including a cell in the cell group as the extraction range.

By this configuration, it is possible to compare the vibration information extracted from the extraction range including the cell group with the vibration information extracted from the extraction range including the cells.

In order to achieve the object, a cell analysis program for operating an information processing apparatus according to an embodiment of the present technology includes an image acquisition unit, a vibration information extraction unit, and a vibration characteristics calculation unit.

The image acquisition unit acquires a cell image by capturing cells at elapsed time.

The vibration information extraction unit extracts vibration information attributable to spontaneous membrane potential vibration of a cell from the cell image.

The vibration characteristics calculation unit calculates vibration characteristics of the vibration information from the vibration information.

In order to achieve the object, a method of analyzing a cell according to an embodiment of the present technology includes capturing at elapsed time a cell to generate a cell image, extracting vibration information attributable to spontaneous membrane potential vibration of a cell from the cell image, and calculating vibration characteristics of the vibration information from the vibration information.

Extracting the vibration information may include extracting the vibration information from a range including one cell in the cell image, and may further include evaluating a type and an intensity of stimulation inputted to the cell based on the vibration characteristics.

Extracting the vibration information may include extracting the vibration information from a range including a cell group including a plurality of cells from the cell image, and may further include evaluating a cell network formation status in the cell group based on the vibration characteristics.

Generating the cell image may include capturing at elapsed time a plurality of cell groups separated by a flow pass that passes only cell neurites but does not pass cell bodies and incubated to generate the cell image.

By the analysis method, it is possible to evaluate a construction of the cell network between the cell groups composed of heterogeneous cells.

As described above, according to the present technology, it is possible to provide a cell analyzer system, a cell analyzing program and a cell analyzing method for effectively evaluating a cell and a cell network.

MODE(S) FOR CARRYING OUT THE INVENTION

A cell analyzer system according to an embodiment of the present technology will be described.

[Configuration of Analyzer System]

Figure 1:
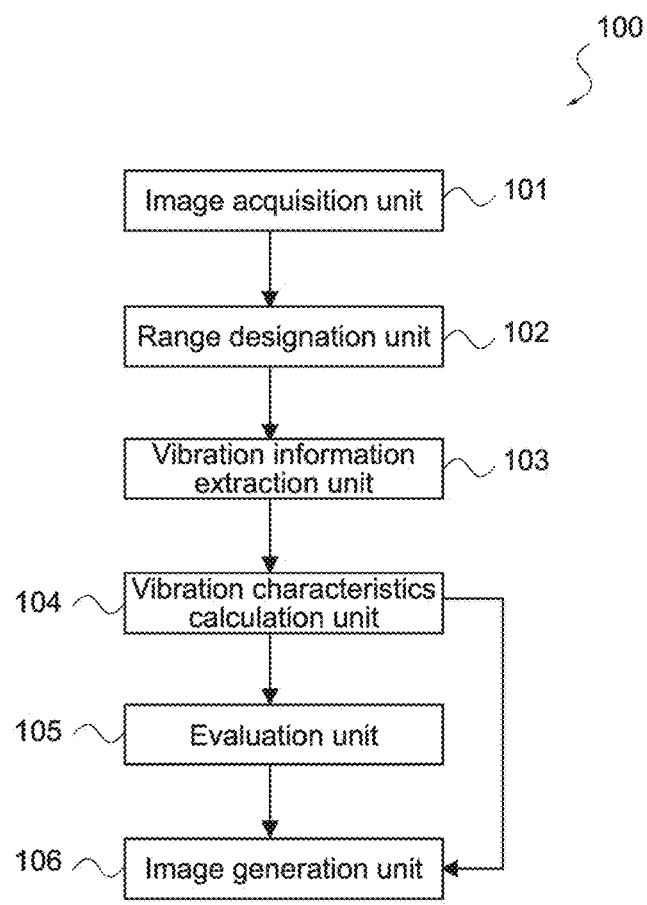
FIG. 1 A schematic diagram showing a configuration of a cell analyzer system according to an embodiment of the present technology.

FIG. 1 is a schematic diagram showing a cell analyzer system 100 according to an embodiment of the present technology. As shown in FIG. 1, the cell analyzer system 100 includes an image acquisition unit 101, a range designation unit 102, a vibration information extraction unit 103, a vibration characteristics calculation unit 104, an evaluation unit 105 and an image generation unit 106. The respective components are functional components driven by an information processing apparatus.

The image acquisition unit 101 acquires an "cell image". The cell image is an image by capturing at elapsed time cells or a cell group to be analyzed, and may be a moving image or a plurality of still images continuously captured. Specifically, the cell image can be captured using a variety of optical image capturing methods such as bright-field image capture, dark-field image capture, phase difference image capture, fluorescence image capture, confocal image capture, multiphoton-excited fluorescence image capture, absorbed light image capture and diffused light image capture.

Figure 2:
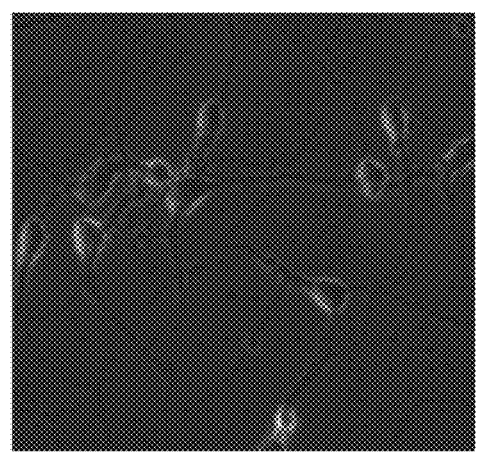
FIG. 2 An illustrative cell image acquired by an image acquisition unit of the cell analyzer system.

FIG. 2 is an illustrative cell image, and is an image including a plurality of neuron cells. The image acquisition unit 101 may acquire the cell image from an image capturing apparatus (a microscopic image capturing apparatus) (not shown), and can acquire the cell image from an image stored in a storage or an image fed through a network. The image acquisition unit 101 feeds the cell image acquired to the range designation unit 102.

Figure 3:
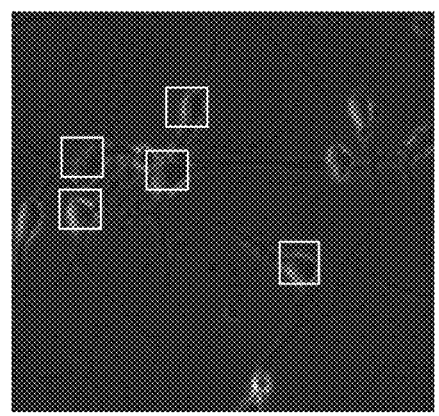
FIG. 3 Illustrative extraction ranges designated by a range designation unit of the cell analyzer system.

The range designation unit 102 designates an "extraction range" in the cell image. The extraction range is a range where the vibration information extraction unit 103 extracts the vibration information as described later. FIG. 3 is illustrative extraction ranges (within square frames in the figure) designated by the range designation unit 102. The range designation unit 102 can designate the extraction range in accordance with an object to be analyzed by a user (such as a cell simple substance and a cell group).

Specifically, if the cell image includes only the cells or the cell group to be analyzed, the range designation unit 102 can designate a whole cell image as the extraction range. If the cell image includes the cells or the cell group to be not analyzed, the range designation unit 102 can designate only a part of the cell image as the extraction range.

If the object to be analyzed is one cell, the range designation unit 102 can designate an image range including the cell as the extraction range. The range designation unit 102 may designate a plurality of the image ranges each of which includes one cell as the extraction range. In FIG. 3, a plurality of the image range each of which includes one cell is designated as the extraction range.

If the object to be analyzed is a cell group including a plurality of cells, the range designation unit 102 can designate the image range including the cell group as the extraction range. Also, the range designation unit 102 may designate a plurality of image ranges each of which includes one cell group as the extraction range. Furthermore, the range designation unit 102 may designate both the image range including the cell group and the image range including the cells of the cell group as the extraction range.

The range designation unit 102 may designate the extraction range by a designation input by a user or may designate the extraction range by detecting the cells or the cell group using image processing. The range designation unit 102 feeds the extraction range designated together with the cell image to the vibration information extraction unit 103.

Figure 4:
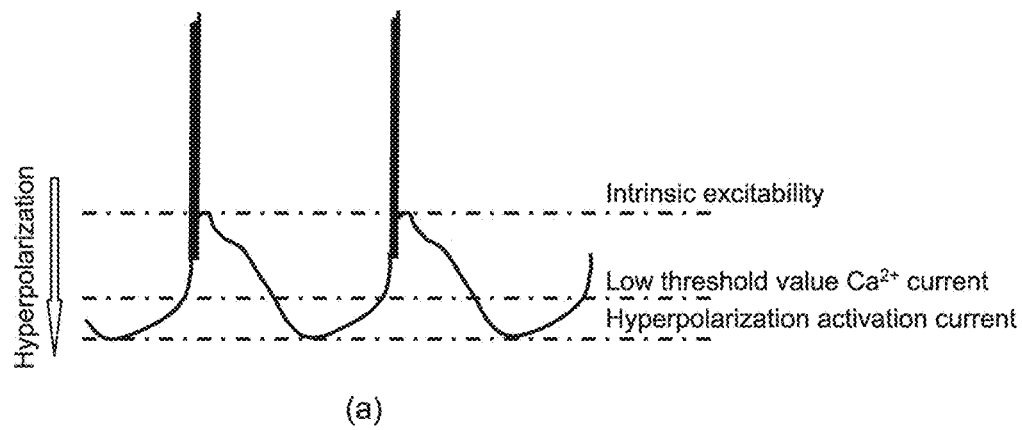
FIG. 4 Schematic diagrams showing spontaneous membrane potential vibration of neuron cells.
Figure 4:
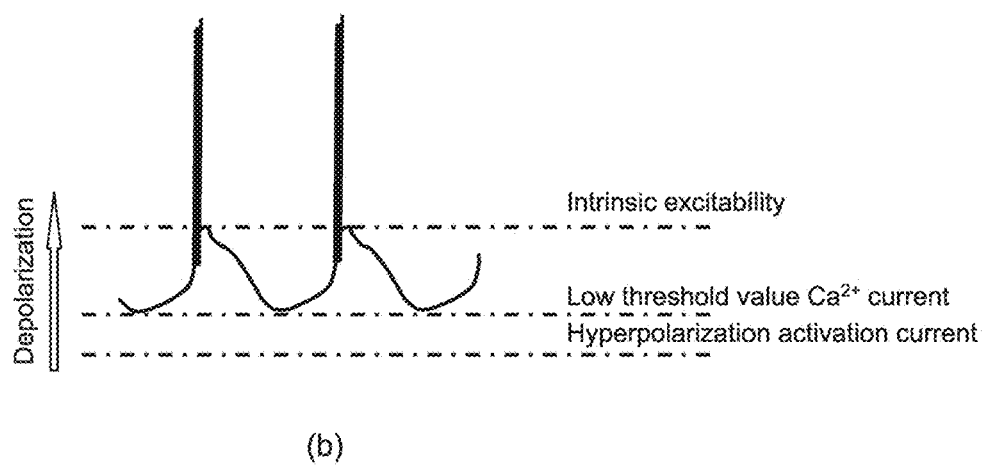
Figure 5:
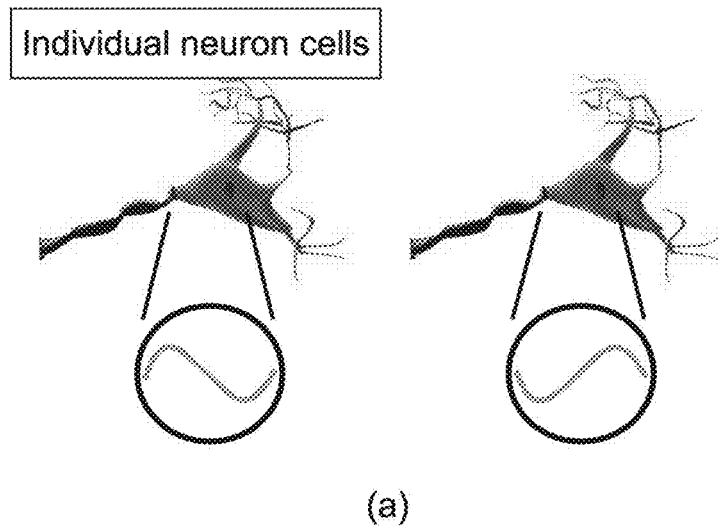
FIG. 5 Schematic diagrams showing synchronization of spontaneous membrane potential vibration accompanied by network formations of neuron cells.
Figure 5:
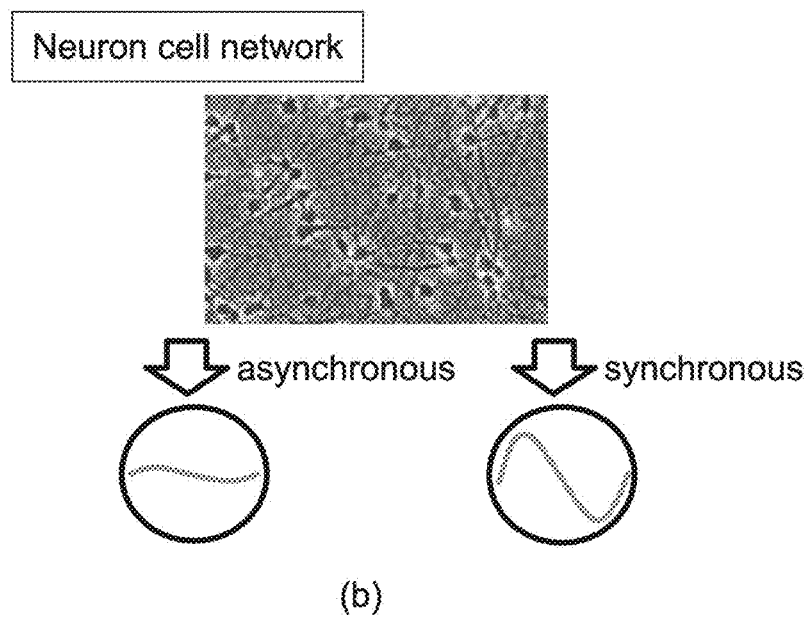

The vibration information extraction unit 103 extracts "vibration information" from the extraction range designated by the range designation unit 102. The vibration information is attributable to spontaneous membrane potential vibration of cells. The spontaneous membrane potential vibration is seen in a part of cells, e.g., neuron cells. Hereinafter, the spontaneous membrane potential vibration will be described taking the neuron cells as an example. FIG. 4 and FIG. 5 are graphs showing the spontaneous membrane potential vibration of neuron cells and showing a change of a membrane potential to the time.

The neuron cells induce the spontaneous membrane potential vibration. Specifically, if no stimulation is inputted from a synapse formed by binding with other neuron cells, a membrane potential is decreased to reach a threshold value, and specific channels act to increase the membrane potential. After the membrane potential caused by an action of the channel has been increased, once it reaches a threshold value where an action potential is generated, the specific channels open to induce the action potential to decrease the film potential again.

Although the threshold value for inducing the action potential is uniform, there is a plurality of combinations of the channels depending on the potential where the membrane potential is changed from decreasing to increasing. An excitability input and an inhibitory input to the neuron cells may change the potential increase.

FIG. 4(*a*) shows the spontaneous membrane potential vibration when the inhibitory input to the neuron cells is great or the excitability input is absent. In this case, as it is directed to hyperpolarization, a deep membrane potential is increased, and the spontaneous membrane potential vibration has a great amplitude and a low frequency. Alternatively, as shown in FIG. 4(*b*), when the excitability input is great or the inhibitory input is absent, a shallow membrane potential is again increased, and the spontaneous membrane potential vibration has a small amplitude and a high frequency. In other words, the spontaneous membrane potential vibration shown in FIG. 4 includes information about a status of the cells such as vitality of the cells, expression and a function of the channel, and a status of stimulation inputted to the cells.

Considering as a neural network composed of a plurality of neuron cells, the potential vibration over a whole network is synchronized by the action potential accompanied by the spontaneous membrane potential vibration, the excitability to connection cells through a synapse or the inhibitory input. FIG. 5 is schematic diagrams showing synchronization of spontaneous membrane potential vibration accompanied by network formations of neuron cells. FIG. 5(*a*) shows the spontaneous membrane potential vibration of individual neuron cells, and FIG. 5(*b*) shows the potential vibration of the neuron cell network composed of a plurality of the neuron cells.

As shown in FIG. 5(*b*), when the network formation is weak ("asynchronous" in the figure), the spontaneous membrane potential vibration of each neuron cell is not in phase, thereby decreasing an amplitude of the potential vibration in the cell group. On the other hand, when the network formation is strong ("synchronous" in the figure), the spontaneous membrane potential vibration of each neuron cell is in phase, thereby increasing the amplitude of the potential vibration in the cell group. In other words, the potential vibration of the cell group shown in FIG. 5(*b*) includes information about a network formation status by the cell group.

As described above, the spontaneous membrane potential vibration of the cells and the potential vibration of the cell group caused by the spontaneous membrane potential vibration reflect the status of the cells and the cell network formation status. The vibration information relates to the vibration caused by the spontaneous membrane potential vibration. Specifically, the vibration information includes vibration of an electromagnetic wave (such as light and radiation) capable of being captured by the image capturing device, e.g., a fluorescence intensity generated from a fluorescent substance fed to the cells, vibration of spectrum frequency or intensity generated from a substance showing optical characteristics (absorption, diffusion, etc.) of the cells, and the like. When the cell image is a bright-field image, a dark-field image, a phase difference image, the vibration information includes vibration information about a cell motion and an intracellular motion provided by an image motion analysis.

Figure 6:
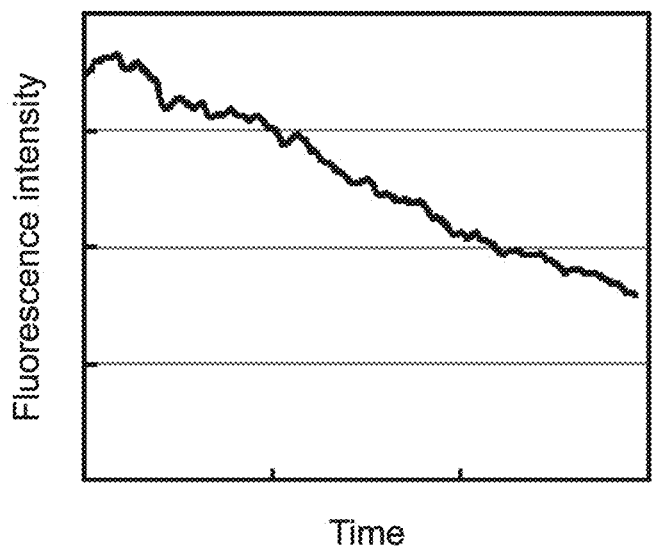
FIG. 6 An illustrative graph of vibration information extracted from a vibration information extraction unit of the cell analyzer system according to an embodiment of the present technology.

The vibration information extraction unit 103 extracts the vibration information from the extraction range of the cell image. Accordingly, the vibration information extracted from the extraction range including one cell is vibration information about the cell, and the vibration information extracted from the extraction range including the cell group is vibration information about the cell group. FIG. 6 is an illustrative graph of the vibration information extracted from the vibration information extraction unit 103, and shows the fluorescence intensity vibration extracted from the extraction range including the neuron cells.

The vibration information extraction unit 103 may extract only one type of vibration information (only the fluorescence intensity vibration, for example) from the extraction range, or may extract a plurality of the vibration information (the fluorescence intensity vibration and the motion vibration, for example). The vibration information extraction unit 103 feeds the extracted vibration information to the vibration characteristics calculation unit 104.

The vibration characteristics calculation unit 104 calculates the "vibration characteristics" from the vibration information. The vibration characteristics are provided by analyzing the vibration information and include information about an amplitude, a frequency and vibration power. Specifically, the vibration characteristics can be represented by a result of a frequency analysis applied to the vibration information such as an FFT (Fast Fourier Transformation) and a wavelet transformation, i.e., a frequency spectrum and a power spectrum.

The vibration characteristics calculation unit 104 may calculate an average value in pixels of the cell image as the vibration characteristics. Specifically, the evaluation unit 105 can calculate as the vibration characteristics the average value in the pixels such as pixels included in the extraction range, pixels where cells are detected, pixels where vibration is detected, pixels where energy from a substance fed to the cells (fluorescent labeling), pixels where characteristic spectra exist and pixels where motion is detected.

Figure 7:
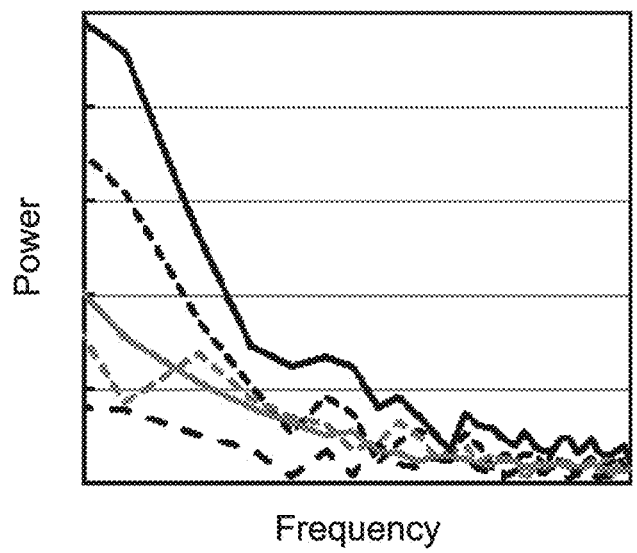
FIG. 7 An illustrative graph of vibration characteristics calculated by a vibration information calculation unit of the cell analyzer system.

FIG. 7 is an illustrative graph of vibration characteristics calculated by a vibration information calculation unit 104, and is a power spectrum provided by applying the FFT to the vibration information (fluorescence intensity vibration)

shown in FIG. 6. The vibration characteristics calculation unit 104 may feed the vibration characteristics calculated to the evaluation unit 105, which may be fed to the image generation unit 106 and be displayed thereon for a user.

The evaluation unit 105 evaluates one cell or a plurality of cells included in the extraction range based on the vibration characteristics fed from the vibration information calculation unit 104. Although the details are described later, the evaluation unit 105 can evaluate a type or a kind of the stimulation inputted to the cell and the formation status of the cell network based on the frequency, the amplitude, the vibration power etc. of the vibration information represented by the vibration characteristics. The evaluation unit 105 may evaluate based on similarities of the vibration characteristics of a plurality of the vibration information (the fluorescence intensity vibration and the motion vibration, for example). The evaluation unit 105 feeds the evaluation result to the image generation unit 106.

The image generation unit 106 generates a display image and displays the image on a display (not shown). The image generation unit 106 may display the vibration characteristics (see FIG. 7) fed from the vibration information calculation unit 104, or may display the evaluation result fed from the evaluation unit 105. The image generation unit 106 may generate the display image by overlapping the cell image with the evaluation result and may display the overlapped one.

The cell analyzer system 100 has the above-described configuration. The configuration of the cell analyzer system 100 is not limited to one information processing apparatus, may be a plurality of the information processing apparatuses, and may be on a network of the information processing apparatuses.

[Behavior of Analyzer System]

The behavior of the analyzer system 100 will be described.

(Evaluation of Cell Simple Substance)

When the cell simple substance is evaluated, the analyzer system 100 behaves as follows:

The image acquisition unit 101 acquires the cell image including the cells to be evaluated, and feeds to the range designation unit 102. The range designation unit 102 designates the range including the cells to be evaluated as the extraction range. The range designation unit 102 can designate the whole cell image as the extraction range if the cell image includes only the cells to be evaluated. The range designation unit 102 may designate a plurality of extraction ranges each of which includes the cells.

The vibration information extraction unit 103 extracts the vibration information from the extraction range as the vibration information (see Embodiments). The vibration information extraction unit 103 may extract a plurality of vibration information, for example, the fluorescence intensity vibration and the motion vibration, from the extraction range. The vibration information calculation unit 104 applies the frequency analysis to the vibration information, and calculates the vibration characteristics.

Here, the vibration information extracted from the extraction range is affected by the spontaneous membrane potential vibration of the cells. Specifically, if the amplitude of the spontaneous membrane potential vibration of the cells is great and the frequency is small, the amplitude of the vibration information generated from the cells becomes also great and the frequency becomes small. If the amplitude of the spontaneous membrane potential vibration of the cells is small and the frequency is great, the amplitude of the vibration information generated from the cells becomes also small and the frequency becomes great.

For this reason, the evaluation unit 107 can evaluate the status of the cells to be evaluated based on the vibration characteristics of the vibration information. Specifically, the evaluation unit 107 evaluates that the inhibitory input to the cells is great or the excitability input is absent in the cells if the amplitude of the vibration information is great and the frequency is small. The evaluation unit 107 evaluates that the excitability input to the cells is great or the inhibitory input is absent in the cells if the amplitude of the vibration information is small and the frequency is great. In addition, the evaluation unit 107 can evaluate the vitality of the cells, the expression and the function of the channel based on the vibration characteristics.

(Evaluation of Cell Network)

When the cell network is evaluated, the analyzer system 100 will behave as follows:

The image acquisition unit 101 acquires the cell image including the cell group to be evaluated, and feeds to the range designation unit 102. The range designation unit 102 designates the range including the cell group to be evaluated as the extraction range. The range designation unit 102 can designate the whole cell image as the extraction range if the cell image includes only the cell group to be evaluated. The range designation unit 102 may designate a plurality of extraction ranges each of which includes the cell group. In addition, the range designation unit 102 can designate the range including the cell group and the range including the cells constituting the cell group as the extraction ranges.

The vibration information extraction unit 103 extracts the vibration information from the extraction range. The vibration information extraction unit 103 may extract a plurality of vibration information, for example, the fluorescence intensity vibration and the motion vibration, from the extraction range. The vibration information calculation unit 104 applies the frequency analysis to the vibration information, and calculates the vibration characteristics.

Here, the vibration information extracted from the cell group is affected by the cell network formation status in the cell group. Specifically, if the cell network formation progresses, the amplitude of the vibration information of the cell group becomes great. If the cell network formation does not progress, the amplitude of the vibration information of the cell group becomes small. This is because the spontaneous membrane potential vibration of each neuron cell synchronizes and is in phase if the cell network formation progresses. On the other hand, the spontaneous membrane potential vibration of each neuron cell is not in phase if the cell network formation does not progress.

For this reason, the evaluation unit 107 can evaluate the cell network formation status in the cell group based on the vibration characteristics extracted from the extraction range including the cell group. Specifically, the evaluation unit 107 evaluates that the cell network formation progresses if the amplitude of the vibration information is great and that the cell network formation does not progress if the amplitude of the vibration information is small.

In addition, the evaluation unit 107 can evaluate the cell network formation status based on a comparison of the vibration characteristics in the vibration information extracted from the extraction range including the cell group and the range including the cells constituting the cell group. This is because the amplitude of the vibration information of the cell group becomes great if the cell network formation progresses, but the vibration information of the cells does not show significant change even though the cell network formation progresses.

In addition, the evaluation unit 107 can evaluate the cell network formation status based on an increase of the amplitude as incubation days go by. This is because the amplitude of the vibration information of the cell group becomes gradually great as the incubation days go by to progress the cell network formation, but the amplitude of the vibration information of the cells does not show significant change even though the cell network formation progresses.

The analyzer system 100 according to the embodiment behaves as described above. Note that a user may operate a part or whole of the behavior of the analyzer system 100 instead of the components of the analyzer system 100.

[Application Embodiment of Present Technology]

Figure 8:
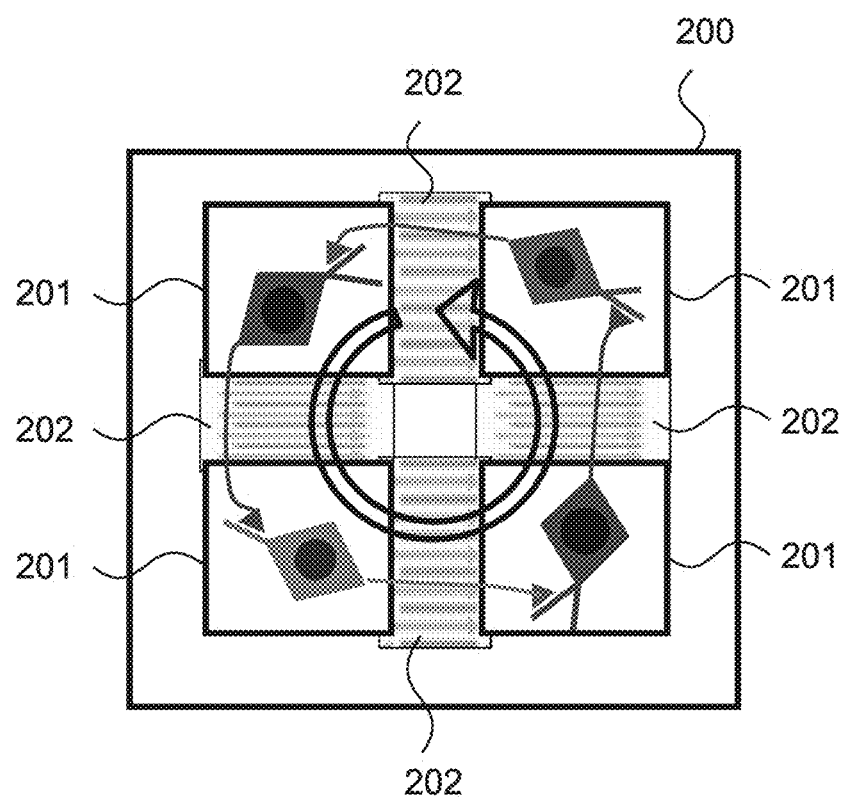
FIG. 8 A schematic diagram of an evaluation plate for a cell network according to an application embodiment of the present invention.

An evaluation system of a neural circuit according to an application embodiment will be described. FIG. 8 is a schematic diagram of an evaluation plate 200 used in the evaluation system of the neural circuit according to the application embodiment of the present technology. The evaluation plate 200 has a plurality of wells 201 for holding the cells. Respective wells 201 are mutually connected by flow paths 202. The flow path 202 passes cell neurites but does not pass cell bodies.

The cell groups having different cell types are incubated in the respective wells 201, and the cell neurites are connected over the flow paths 202. The respective wells 201 are image-captured at elapsed time to provide cell images. Based on the cell images, the cell network formation status is evaluated as described above. It is thus possible to evaluate the cell network formation status between different cell types.

Different from an optical observation, the cell group distributed in a perpendicular direction can be evaluated by scanning a focal plane in a perpendicular direction. Also, it is possible to form a concentration gradient of a physiological active substance or a pharmaceutical drug acting on the cells and to evaluate along with the concentration gradient. In addition, the cell group excluding the neuron cells may be incubated in the respective wells 201 at the same time to evaluate the cell network formation status.

The present technology is not limited to the above-described embodiments, and variations modifications may be made without departing from the scope of the present technology.

[Embodiments]

[1. $Ca^{2+}$ Influx Vibration]

(1-1. Effect of Physiological Active Substance on Fluorescence Intensity Vibration of Neuron Cells)

Effects of GABA and L-Glu on the neuron cells and the neuron cell network were evaluated using the fluorescence intensity vibration. The GABA is a physiological active substance that gives inhibitory stimulation to the neuron cells. The L-Glu gives exciting stimulation.

Fluo8 (fluorescent labeling) used in $Ca^{2+}$ imaging was entrained in the neuron cells (iPS Academia Japan) that were differentiation of iPS cells. The GABA or the L-Glu was administered to incubation liquid. Fluorescence of the Fluo8 generated from each neuron cell was image-captured at 2 flame/sec for 1 minute to provide each cell image.

Figure 9:
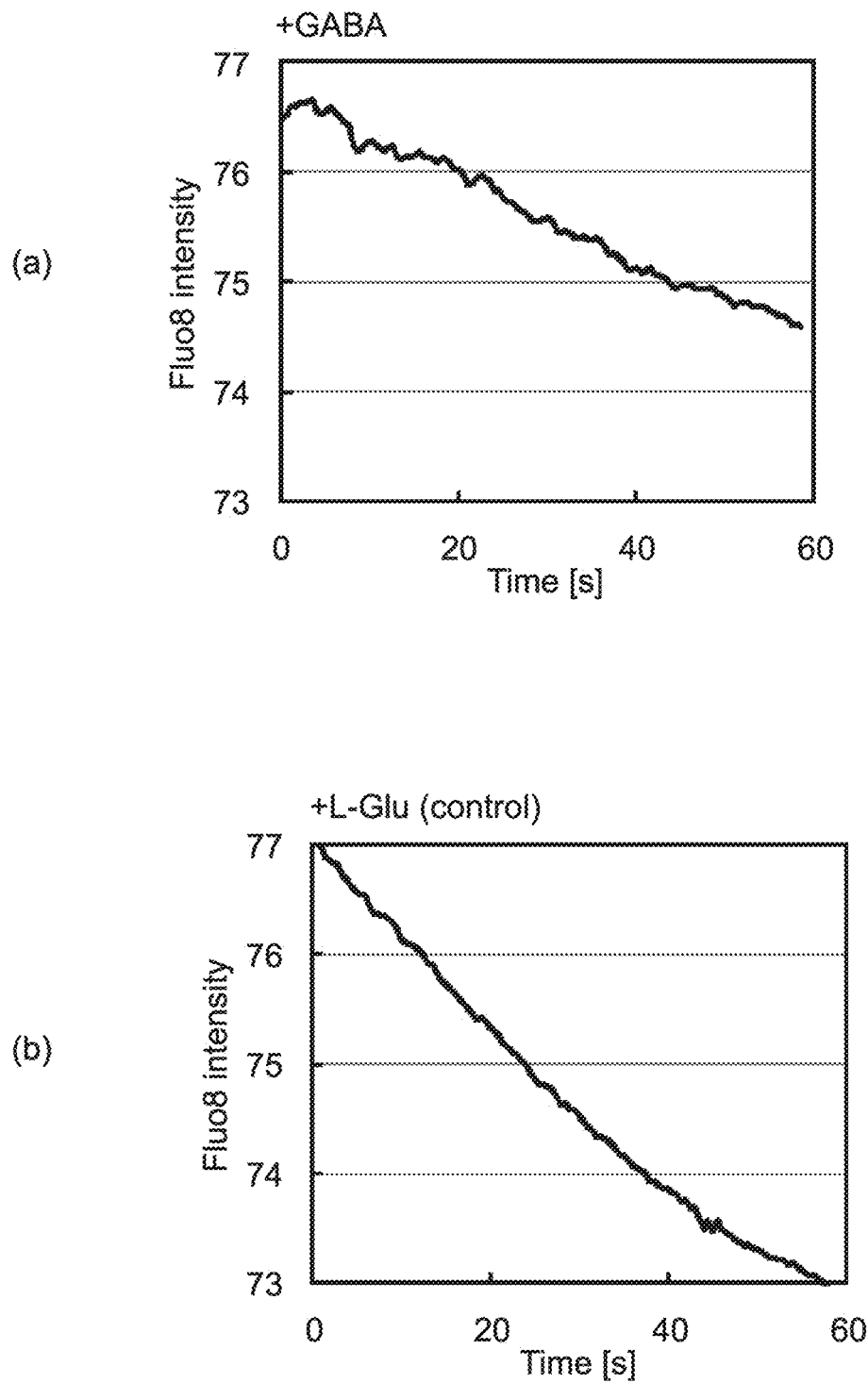
FIG. 9 Graphs of fluorescence intensity vibration extracted from an extraction range including neuron cells to which a physiological active substance is administrated according to an embodiment of the present invention.

The fluorescence intensity vibration (vibration information) was extracted from each cell image, taking the image range including one neuron cell as the extraction range. FIG. 9(a) is a graph of fluorescence intensity vibration extracted from the cell image of the neuron cells to which the GABA is administered. FIG. 9(b) is a graph of fluorescence intensity vibration extracted from the cell image of the neuron cells to which the L-Glu is administered.

Figure 10:
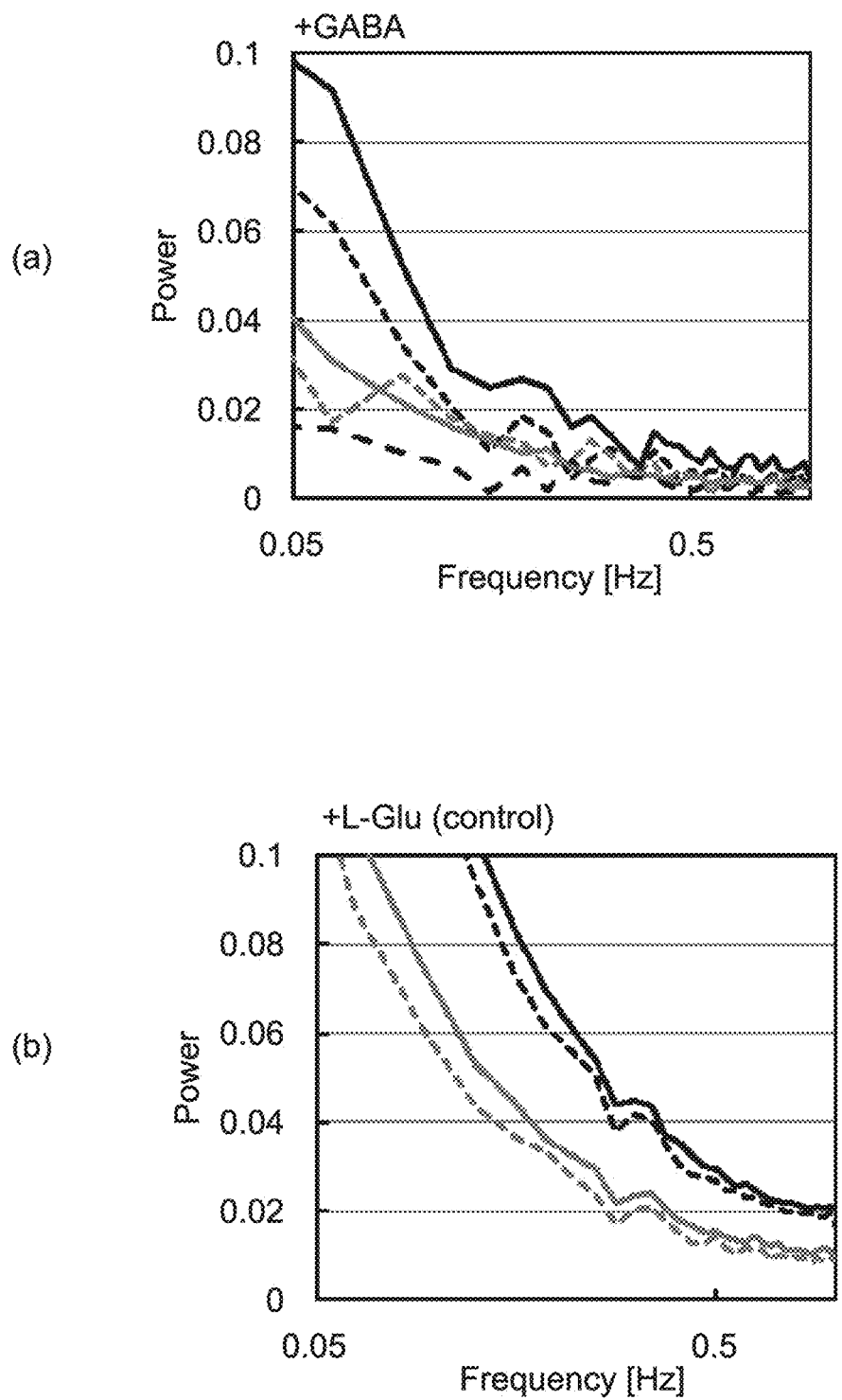
FIG. 10 Graphs of vibration characteristics of fluorescence intensity vibration extracted from an extraction range including neuron cells to which a physiological active substance is administrated according to an embodiment of the present invention.

Then, the FFT analysis was applied to fluorescence intensity vibration to calculate power spectra (vibration characteristics). FIG. 10(a) is a graph of power spectrum calculated from the fluorescence intensity vibration (FIG. 9(a)) of the neuron cells to which the GABA is administered. FIG. 10(b) is a graph of power spectrum calculated from the fluorescence intensity vibration (FIG. 9(a)) of the neuron cells to which the L-Glu is administered.

When the power spectra shown in FIGS. 10(a) and 10(b) are compared, it is found that the fluorescence intensity vibration of the neuron cells to which the GABA is administered has the amplitude greater and the frequency lower than those of the fluorescence intensity vibration of the neuron cells to which the L-Glu is administered. In other words, by administrating the GABA and L-Glu, the spontaneous membrane potential vibration of the neural cells is changed, which can be confirmed by the vibration characteristics of the fluorescence intensity vibration.

(1-2. Change in Fluorescence Intensity Vibration of Cell Group by Neural Cell Network Formation)

In the neuron cells (iPS Academia Japan) that were differentiation of iPS cells, a cell group where no neural cell network was formed and a cell group where the neural cell network was formed were prepared. Fluo8 was entrained in each cell group. Fluorescence of the Fluo8 generated from each neuron cell was image-captured at 2 flame/sec for 1 minute to provide each cell image.

Figure 11:
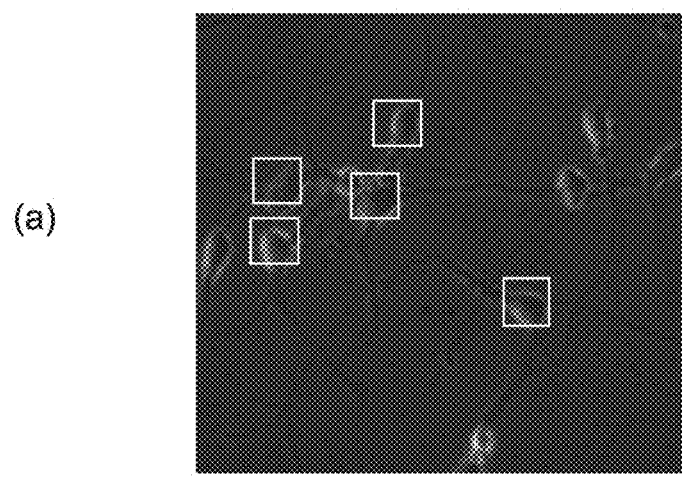
FIG. 11 Cell images according to the embodiment of the present invention.
Figure 11:
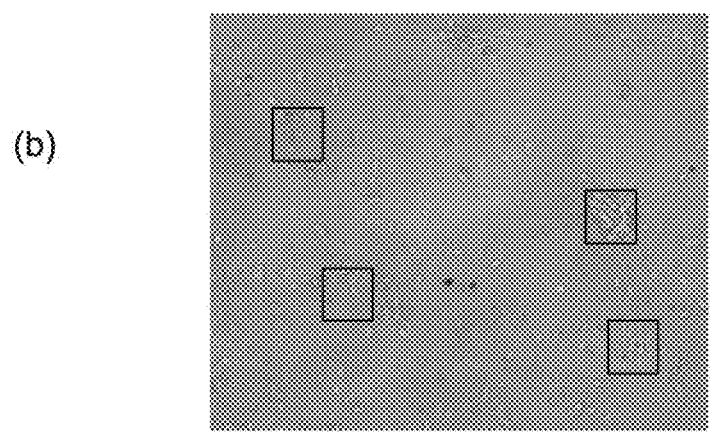
Figure 12:
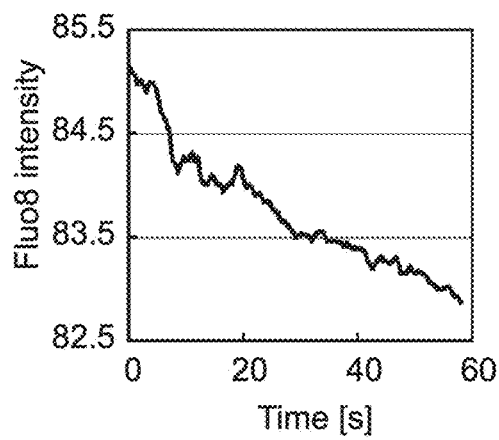
FIG. 12 Graphs of fluorescence intensity vibration extracted from an extraction range including individual cells forming no cell network according to an embodiment of the present invention.
Figure 12:
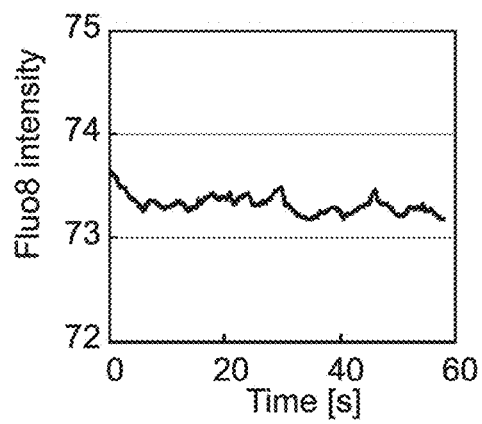
Figure 12:
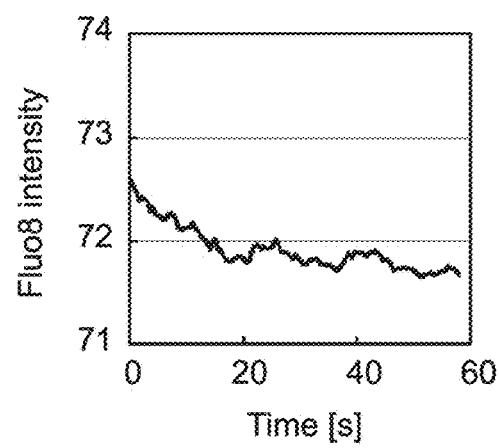
Figure 12:
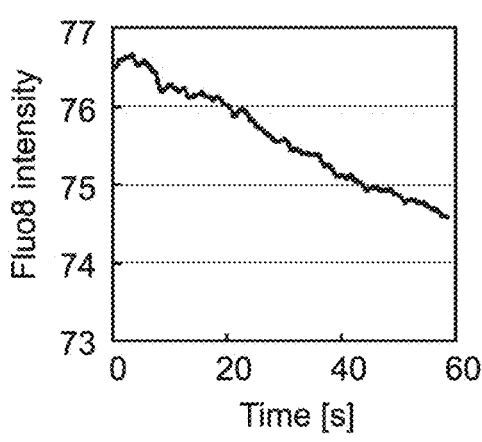

FIG. 11(a) is a cell image of the cell group where no neural cell network was formed and FIG. 11(b) is a cell image of the cell group where the neural cell network was formed. In each cell image, the image range including a whole image and one neural cell is used as the extraction range to extract the fluorescence intensity vibration. FIG. 11(a) and FIG. 11(b) show the extraction ranges each including one neural cell (within framed boxes in the figures).

Figure 13:
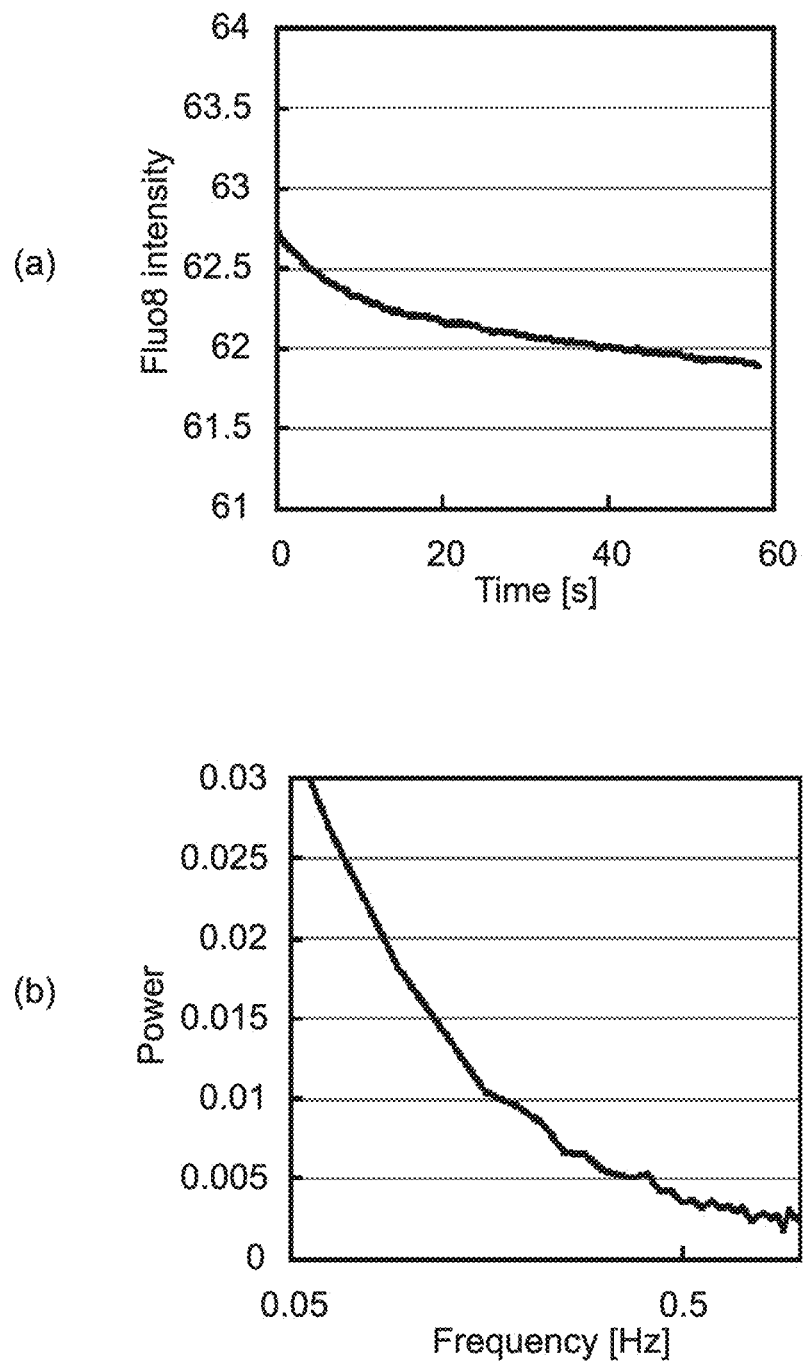
FIG. 13 Graphs of fluorescence intensity vibration and vibration characteristics extracted from an extraction range including cells forming no cell network according to an embodiment of the present invention.
Figure 14:
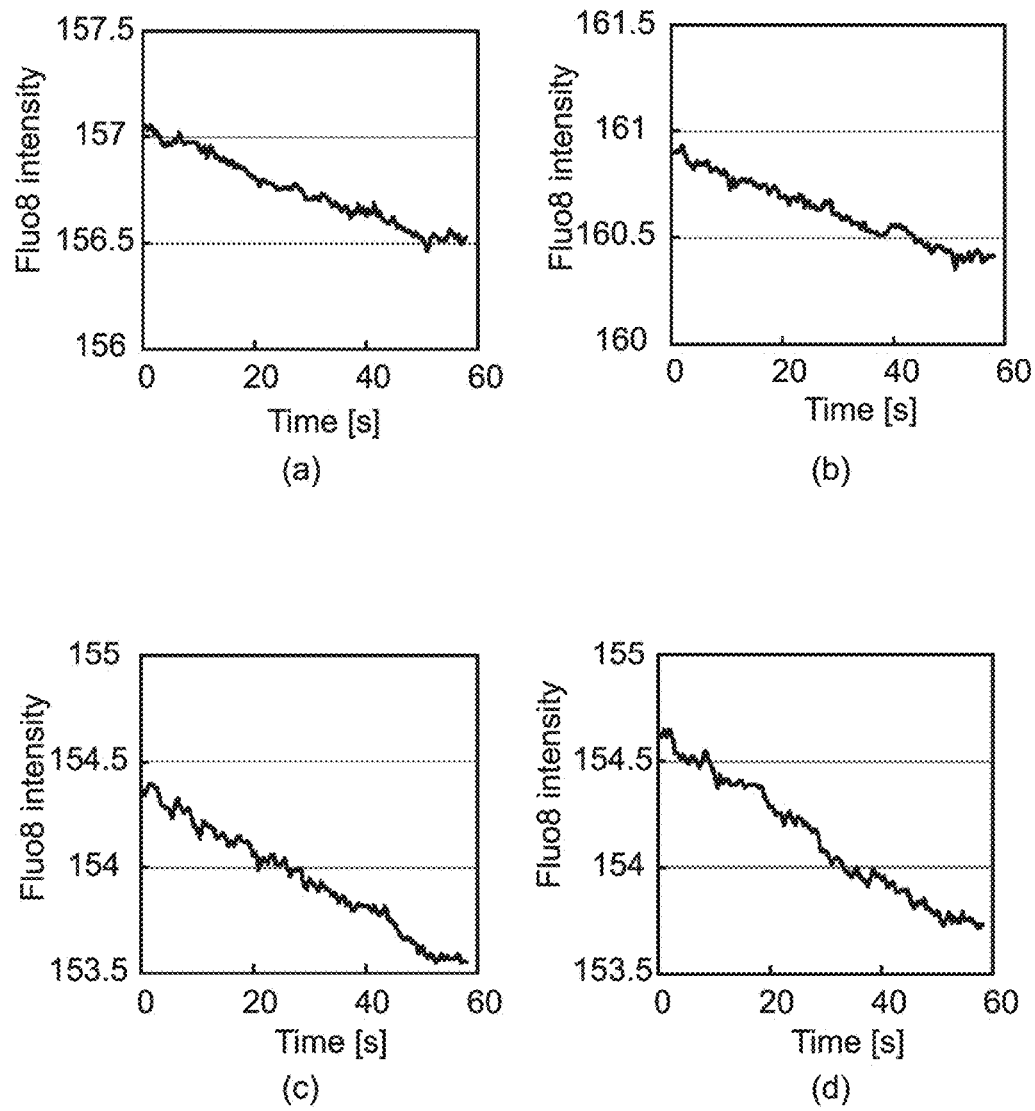
FIG. 14 Graphs of fluorescence intensity vibration extracted from an extraction range including individual cells forming a cell network according to an embodiment of the present invention.

The fluorescence intensity vibration (vibration information) was extracted from the extraction range (the whole image and each cell) of the cell image (FIG. 11(a)) of the cell group where no neural cell network was formed. FIGS. 12(a) to (d) are graphs of the fluorescence intensity vibration of each cell in the same cell group. FIG. 13(a) is a graph of the fluorescence intensity vibration of the whole image (cell group). Power spectra (vibration characteristics) of the fluorescence intensity vibration of the whole image (FIG. 13(a)) were calculated. The power spectra are shown in FIG. 13(b).

While the vibration was observed in FIGS. 12(a) to (d) showing the fluorescence intensity vibration of each cell, little vibration was observed in FIG. 13(a) showing the fluorescence intensity vibration of the cell group as apparent from the FIG. 13(b) showing the power spectra.

Figure 15:
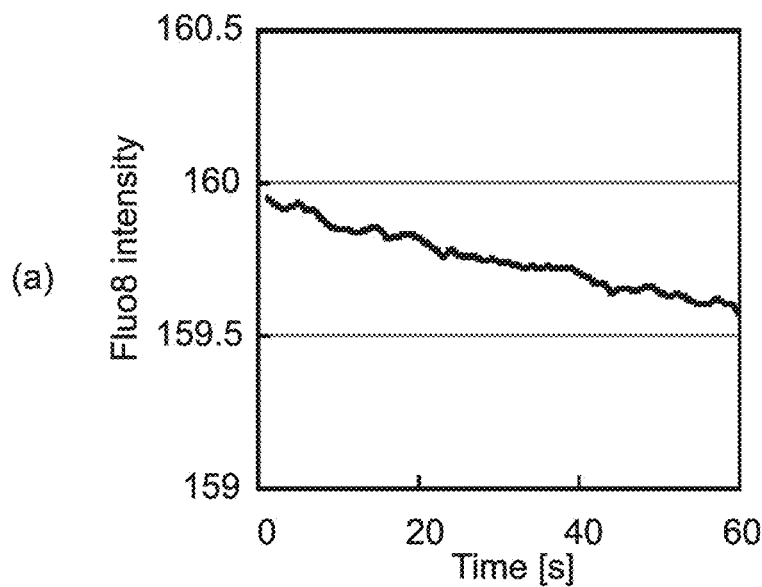
FIG. 15 Graphs of fluorescence intensity vibration and vibration characteristics extracted from an extraction range including individual cells forming a cell network according to an embodiment of the present invention.
Figure 15:
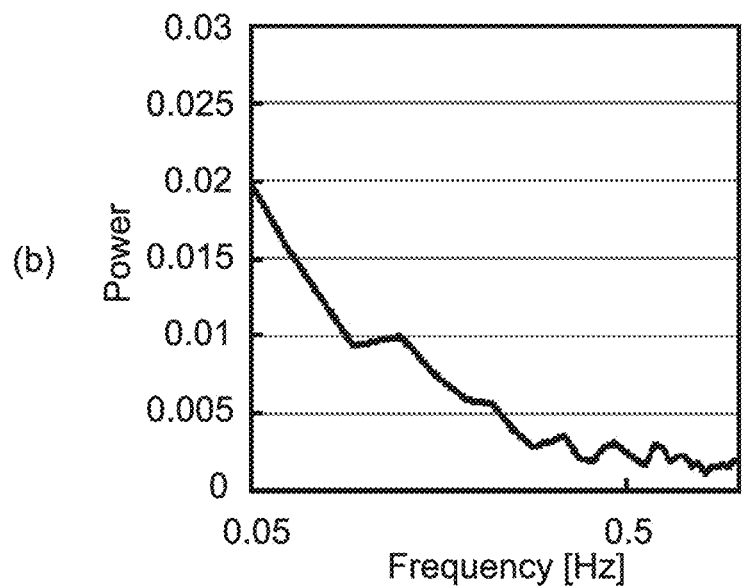
Figure 16:
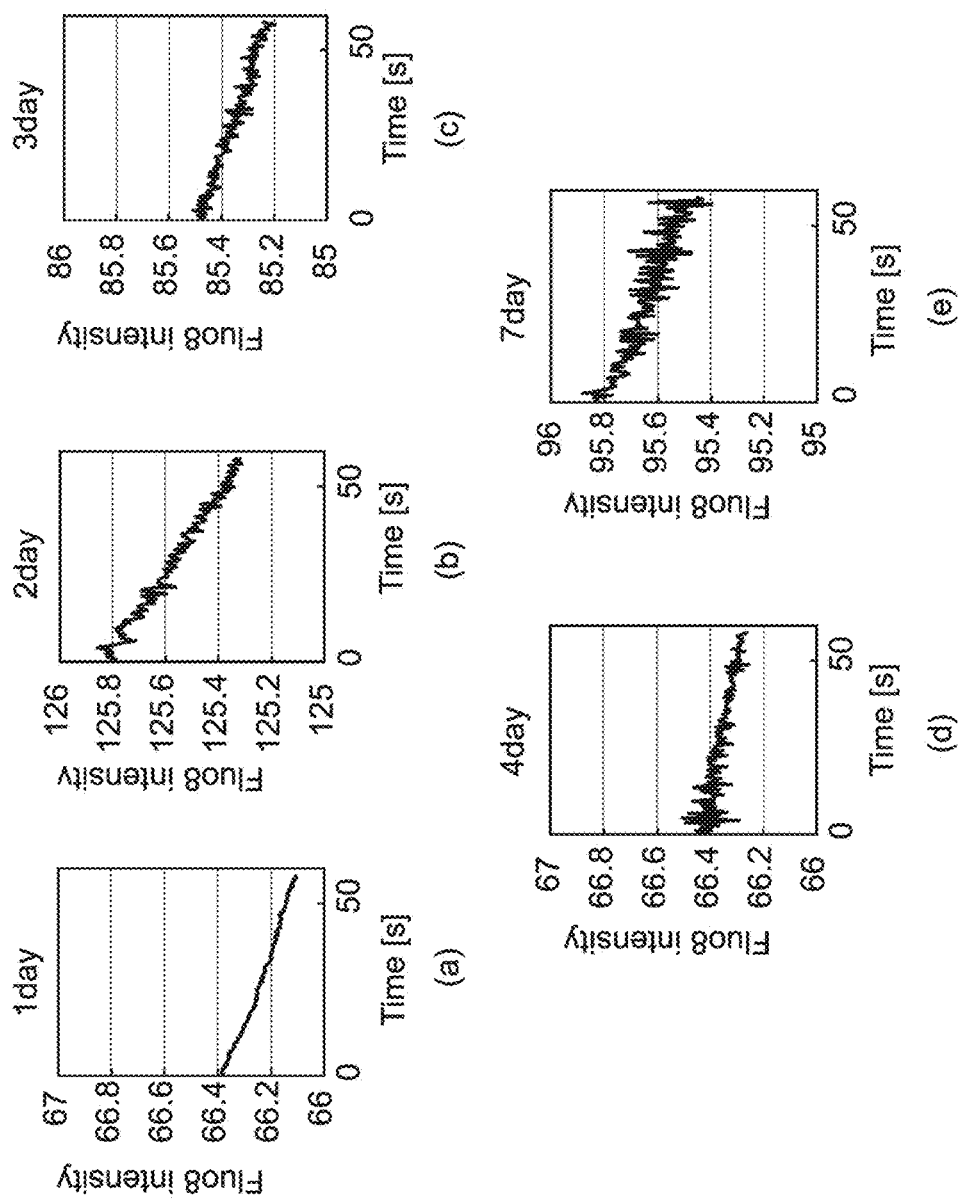
FIG. 16 Graphs of fluorescence intensity vibration extracted from an extraction range including a cell group per incubation day according to an embodiment of the present invention.
Figure 17:
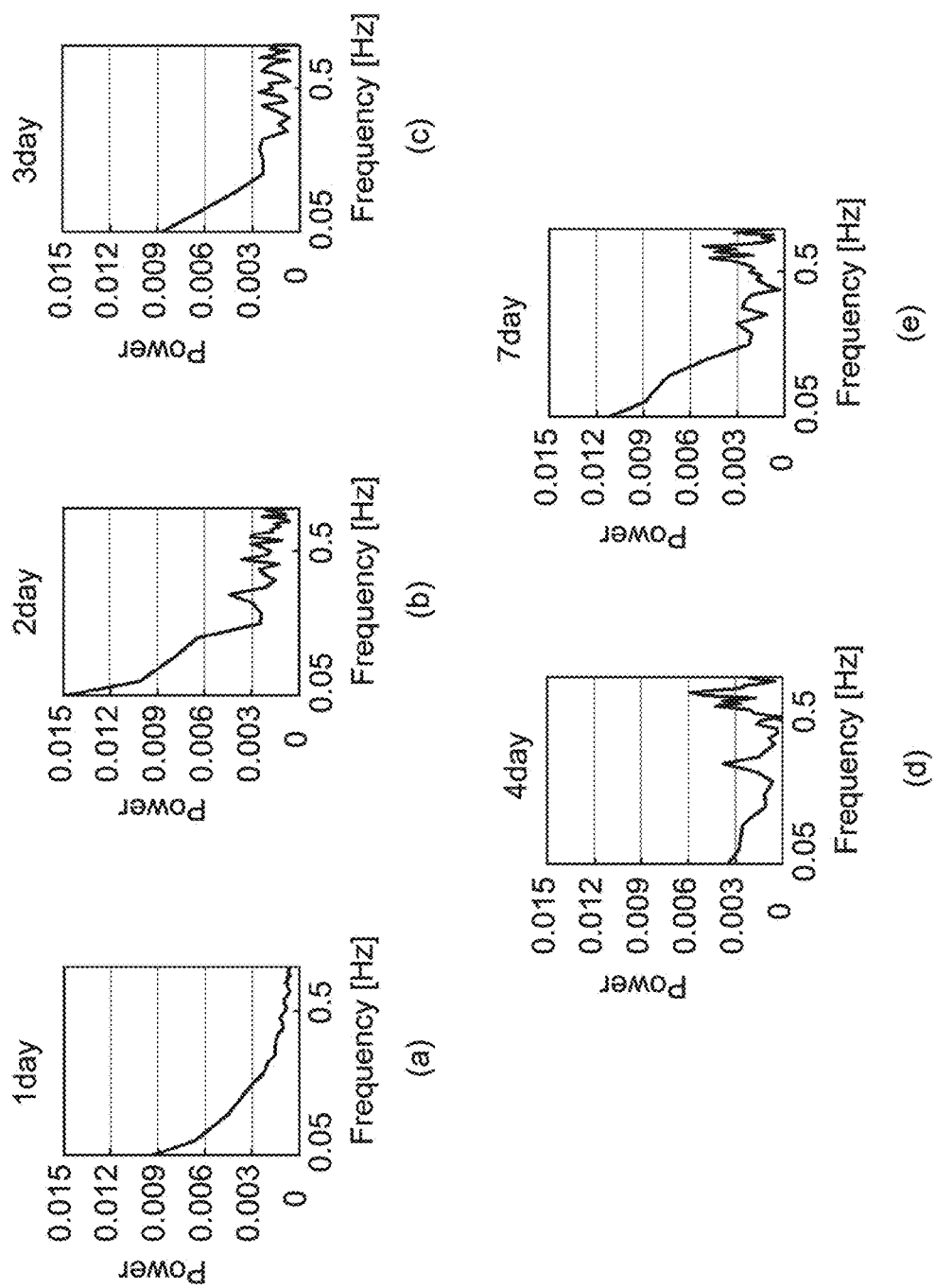
FIG. 17 Graphs of vibration characteristics of fluorescence intensity vibration extracted from an extraction range including a cell group per incubation day according to an embodiment of the present invention.
Figure 18:
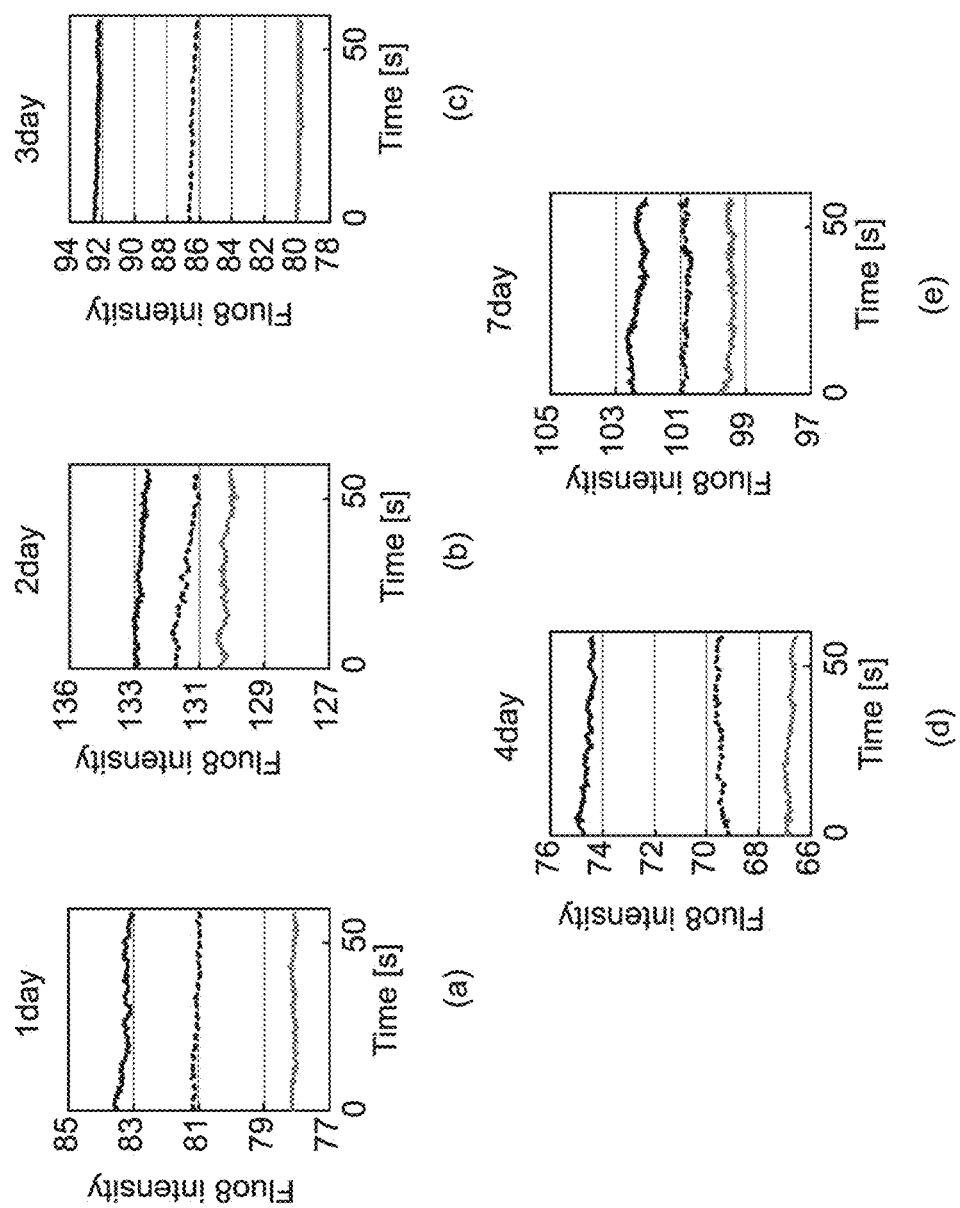
FIG. 18 Graphs of fluorescence intensity vibration extracted from an extraction range including individual cells per incubation day according to an embodiment of the present invention.
Figure 19:
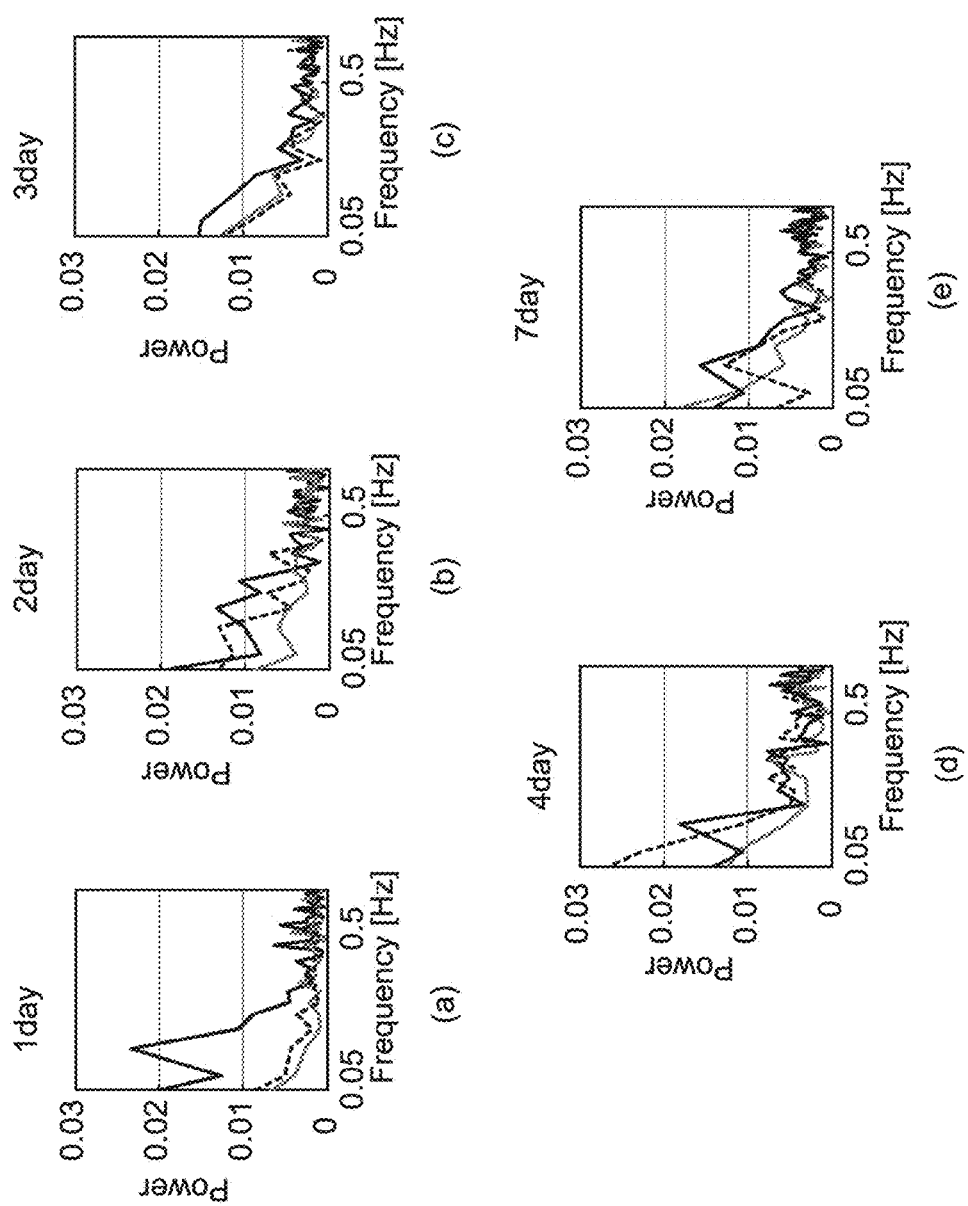
FIG. 19 Graphs of vibration characteristics of fluorescence intensity vibration extracted from an extraction range including individual cells per incubation day according to an embodiment of the present invention.

The fluorescence intensity vibration (vibration information) was extracted from the extraction range (the whole image and each cell) of the cell image (FIG. 11(b)) of the cell group where the neural cell network was formed. FIGS. 14(a) to (d) are graphs of the fluorescence intensity vibration of each cell in the same cell group. FIG. 15(a) is a graph of the fluorescence intensity vibration of the whole image (cell group). Power spectra (vibration characteristics) of the fluorescence intensity vibration of the whole image (FIG. 15(a)) were calculated. The power spectra are shown in FIG. 15(b).

The vibration was observed in FIGS. 14(a) to (d) showing the fluorescence intensity vibration of each cell, the vibration was observed similar to the case where no neural cell network was formed (FIGS. 13(a) to (d)). Also, the vibration was observed in FIG. 15(a) showing the fluorescence intensity vibration of the cell group as apparent from the FIG. 15(b) showing the power spectra.

This reveals that the vibration is observed in the fluorescence intensity vibration of each cell in spite of the presence or absence of the formation of the neural cell network, but the fluorescence intensity vibration of the cell group is affected by the presence or absence of the formation of the neural cell network. In other words, based on the vibration characteristics of the fluorescence intensity vibration from the cell group as the extraction range, it can be evaluated whether or not the cell group forms the neural cell network.

Then, the cell group where no neural cell network was formed was incubated for seven days to observe the change in the fluorescence intensity vibration accompanied by the formation of the neural cell network. FIGS. 16(a) to (e) are graphs of the fluorescence intensity vibration extracted from the extraction range including the cell group per incubation day. FIGS. 17(a) to (e) are graphs of the power spectra calculated from the fluorescence intensity vibration of the cell group (FIGS. 16(a) to (e)).

As shown in FIGS. 17(a) to (e), the vibration power in the fluorescence intensity vibration is increased as the incubation days go by, and the changes after one day and two days from the incubation are especially great. It shows that the neural cell network is formed as the incubation days go by, and the synchronization of the spontaneous membrane potential vibration in each cell progresses. Also, it shows that the formation of the neural cell network progresses after one day and two days from the incubation.

On the other hand, FIGS. 18(a) to (e) are graphs of the fluorescence intensity vibration extracted from the extraction range including individual cells of the cell group per incubation day. FIGS. 19(a) to (e) are graphs of the power spectra calculated from the fluorescence intensity vibration of the individual cells (FIGS. 18(a) to (e)).

As shown in FIGS. 19(a) to (e), the vibration power in the fluorescence intensity vibration is not significantly changed as the incubation days go by. As described above, the vibration power in the fluorescence intensity vibration of the cell group is increased. It can be confirmed that the vibration power in the fluorescence intensity vibration of the cell group reflects the formation of the neural cell network.

[2. Motion Vibration]

(2-1. Comparison of Motion Vibration and Fluorescence Excitation Vibration in Neural Cells)

In the cell image provided by capturing the neural cells derived from iPS cells at 2 flame/sec for 1 minute, the motion vibration (vibration information) was extracted utilizing the motion analysis by block matching from the extraction range including the neural cells. From each extraction range, the fluorescence intensity vibration (vibration information) was extracted by the above-described $Ca^{2+}$ imaging.

Figure 20:
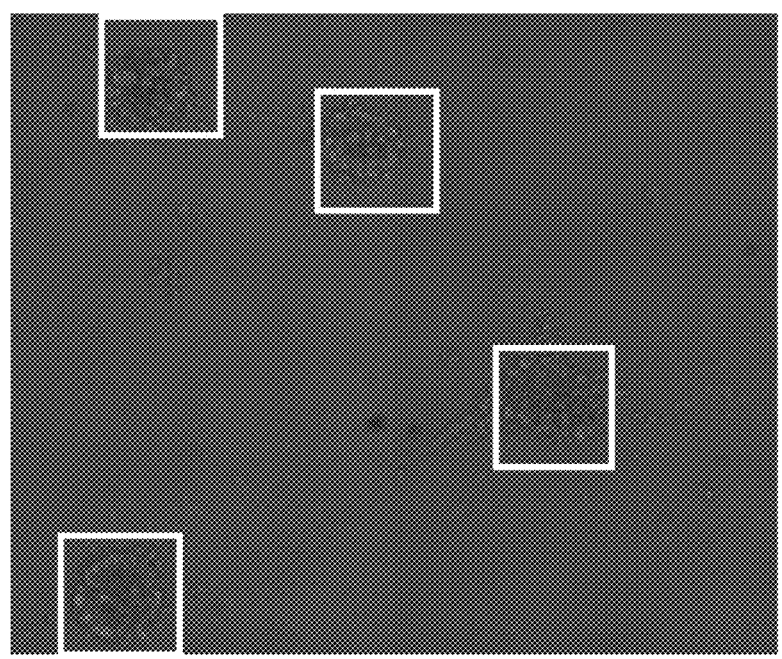
FIG. 20 A cell image according to an embodiment of the present invention.
Figure 21:
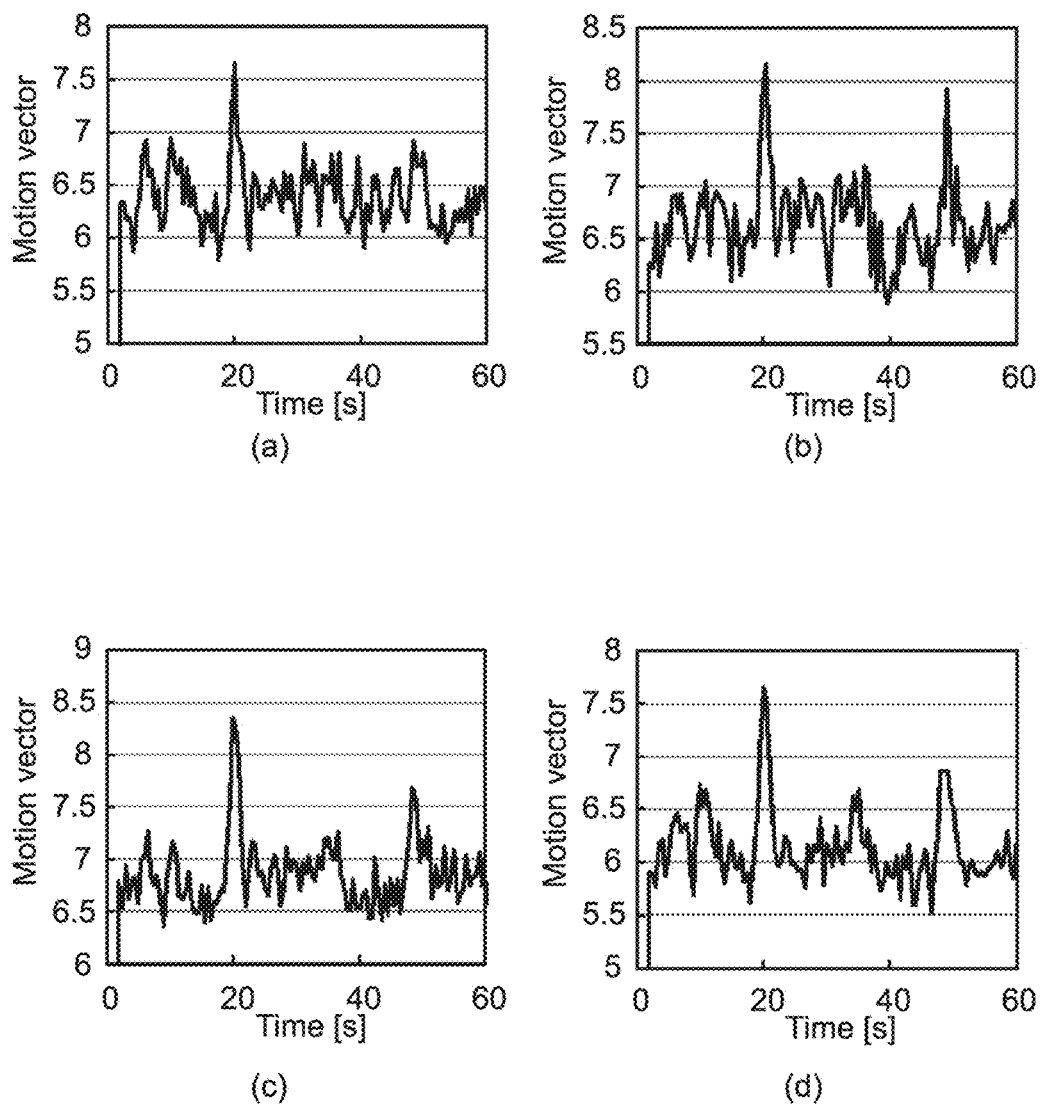
FIG. 21 Graphs of motion vibration extracted from an extraction range including individual cells according to an embodiment of the present invention.
Figure 22:
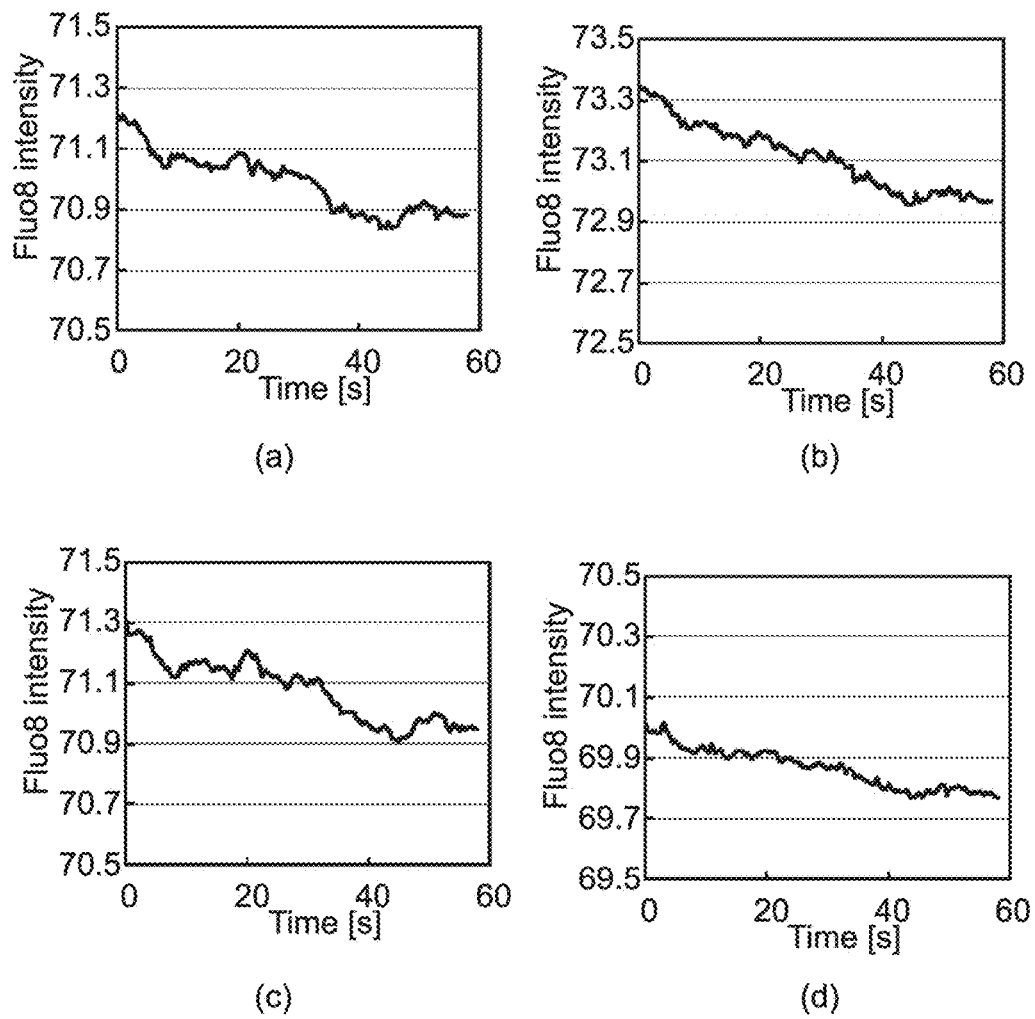
FIG. 22 Graphs of fluorescence intensity vibration extracted from an extraction range including individual cells according to an embodiment of the present invention.

FIG. 20 shows the cell image and the extraction range (within square frames in the figure). FIGS. 21(a) to (d) are graphs showing the motion vibration extracted from each extraction range, and FIGS. 22(a) to (d) are graphs showing the fluorescence intensity vibration extracted from each extraction range. FIG. 21(a) and FIG. 22(a), FIG. 21(b) and FIG. 22(b), FIG. 21(c) and FIG. 22(c), FIG. 21(d) and FIG. 22(d) are extracted from the same extraction range, respectively.

When the motion vibration (FIG. 21) and the fluorescence intensity vibration (FIG. 22) are compared, the respective vibration characteristics are not fully matched, but partially correlated waveforms are shown. It can be concluded that at least a part of the motion vibration of the neural cells is controlled by the $Ca^{2+}$ influx.

(2-2. Effect of Physiological Active Substance on Motion Vibration of Neuron Cells)

Effects of GABA and L-Glu administered on the neuron cells were evaluated. The GABA or the L-Glu was administered to incubation liquid of the neuron cells (iPS Academia Japan) that were differentiation of iPS cells. Each neuron cell was image-captured at 2 flame/sec for 1 minute to provide each cell image.

Figure 23:
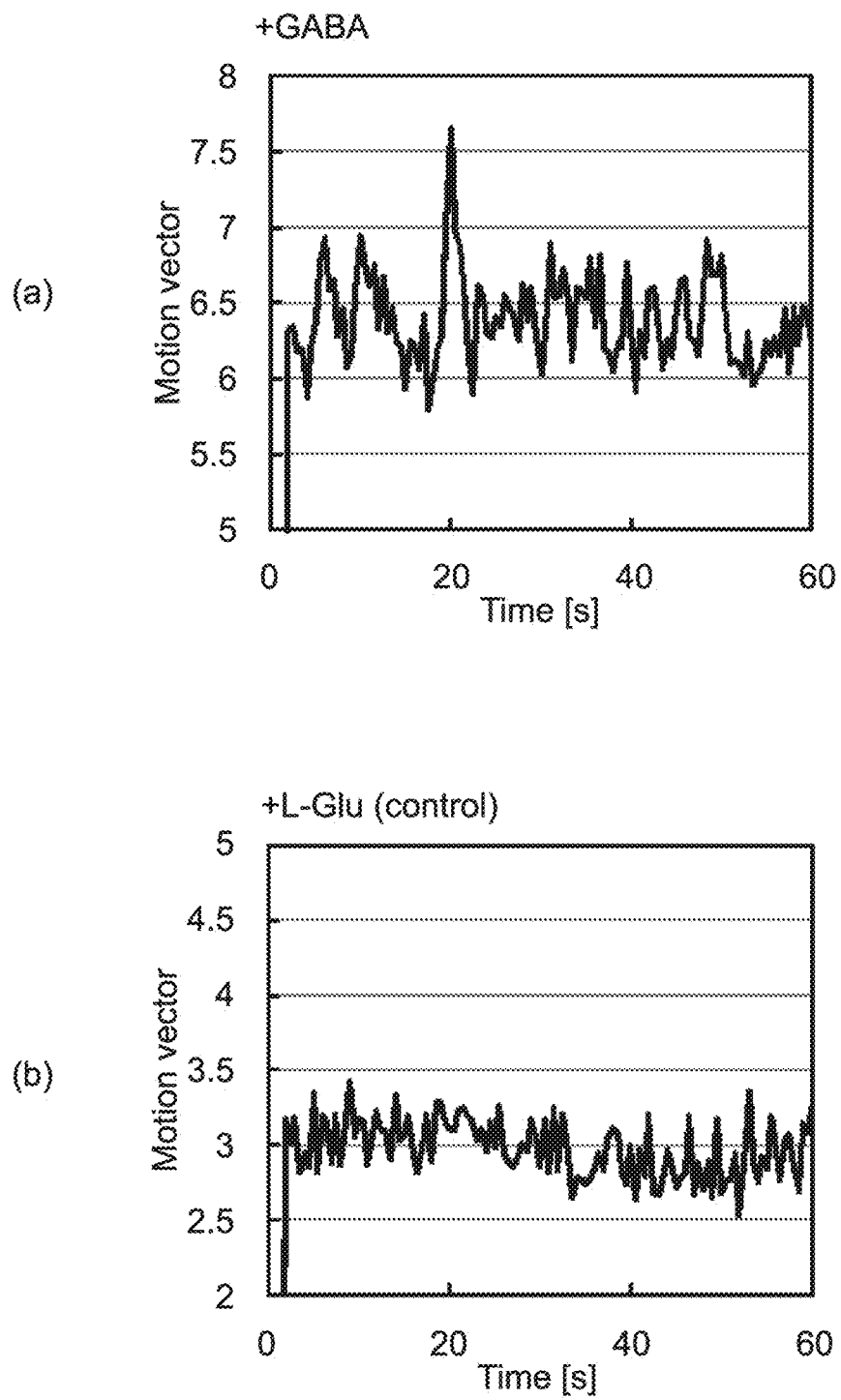
FIG. 23 Graphs of motion vibration extracted from an extraction range including neuron cells to which a physiological active substance is administrated according to an embodiment of the present invention.

In each cell image, the motion vibration was extracted using the image range including one neuron cell as the extraction range. FIG. 23(a) is a graph of the motion vibration extracted from the cell image of the neural cells to which the GABA is administrated. FIG. 23(b) is a graph of the motion vibration extracted from the cell image of the neural cells to which the L-Glu is administrated.

Figure 24:
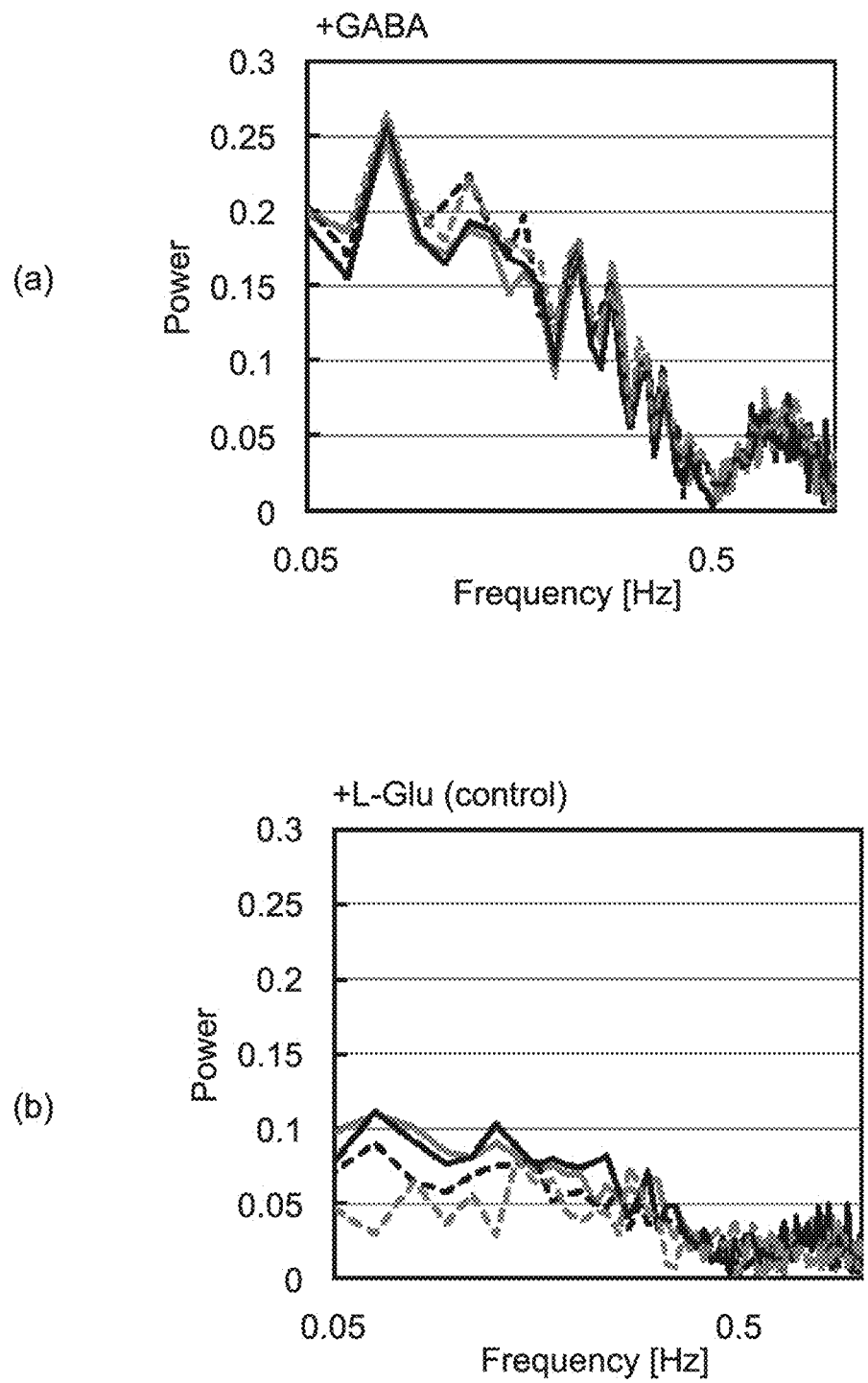
FIG. 24 Graphs of vibration characteristics of motion vibration extracted from an extraction range including neuron cells to which a physiological active substance is administrated according to an embodiment of the present invention.
Figure 25:
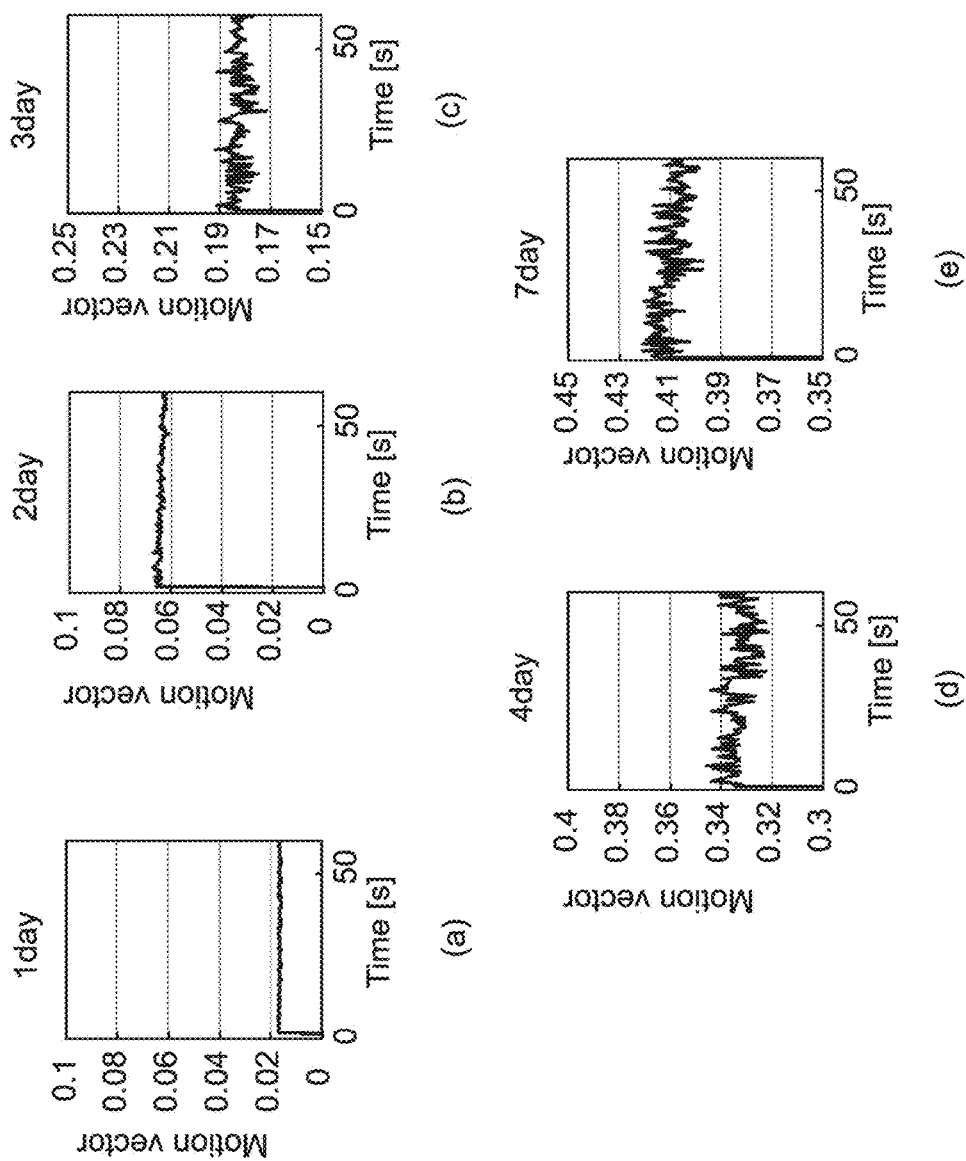
FIG. 25 Graphs of fluorescence intensity vibration extracted from an extraction range including a cell group per incubation day according to an embodiment of the present invention.

Then, the FFT analysis was applied to the motion vibration to calculate power spectra. FIG. 24(a) is a graph of power spectrum calculated from the motion vibration (FIG. 23(a)) of the neuron cells to which the GABA is administered. FIG. 24(b) is a graph of power spectrum calculated from the motion vibration (FIG. 23(b)) of the neuron cells to which the L-Glu is administered.

When the power spectra shown in FIGS. 24(a) and 24(b) are compared, it is found that the motion vibration of the neuron cells to which the GABA is administered has the amplitude greater and the frequency lower than those of the motion vibration of the neuron cells to which the L-Glu is administered. In other words, by administrating the GABA and L-Glu, the spontaneous membrane potential vibration of the neural cells is changed, which can be confirmed by the vibration characteristics of the motion vibration.

(2-3. Change in Motion Vibration of Cell Group by Neural Cell Network Formation)

Figure 26:
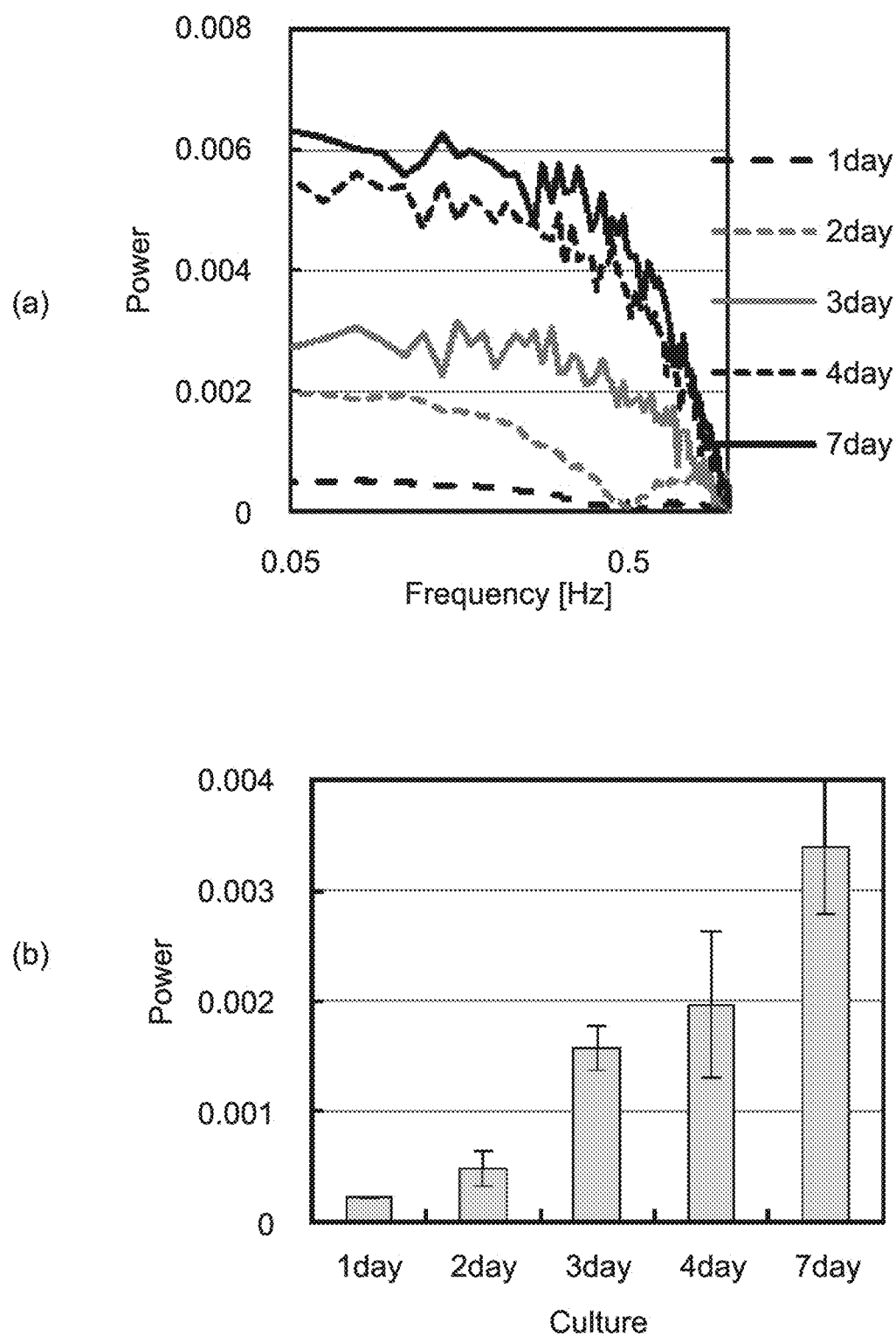
FIG. 26 Graphs of vibration characteristics of motion vibration and average values of vibration magnitudes extracted from an extraction range including a cell group per incubation day according to an embodiment of the present invention.

In the neuron cells (iPS Academia Japan) that were differentiation of iPS cells, a cell group where no neural cell network was formed was incubated for seven days to observe the change in the motion vibration accompanied by the formation of the neural cell network. FIGS. 25(a) to (e) are graphs of the motion vibration extracted from the whole image including the cell group as the extraction range per incubation day. FIG. 26(a) is a graph of the power spectra calculated from the motion vibration of the cell group (FIGS. 25(a) to (e)), and FIG. 26(b) is a graph showing average values of the vibration power in each pixel included in the extraction range in each culture day.

As shown in FIG. 26(a) and FIG. 26(b), the vibration power in the motion vibration is increased as the incubation days go by. It shows that the neural cell network is formed as the incubation days go by, and the synchronization of the spontaneous membrane potential vibration in each cell progresses. In other words, it is possible to evaluate a degree of the network formation using the motion vibration of the cell group.

(2-4. Evaluation of Cytotoxicity by Motion Vibration)

Effects of a cytotoxic substance administered on the neuron cells were evaluated using the motion vibration of the cells. As a cytotoxic model, the cytotoxicity of Aβ peptide considered as a cause of the Alzheimer disease and a neuroprotective action of an anti-alzheimer's disease drug, i.e., memantine were evaluated. As the cytotoxicity of Aβ peptide, there are a synapse failure by acting on synapses and a cell failure entrained in the cells.

The cell group of the neural cells derived from iPS cells where a sufficient neural cell network was formed was prepared. A predetermined amount of Aβ peptide or Aβ peptide and memantine was administered to each cell group to incubate for five days.

Figure 27:
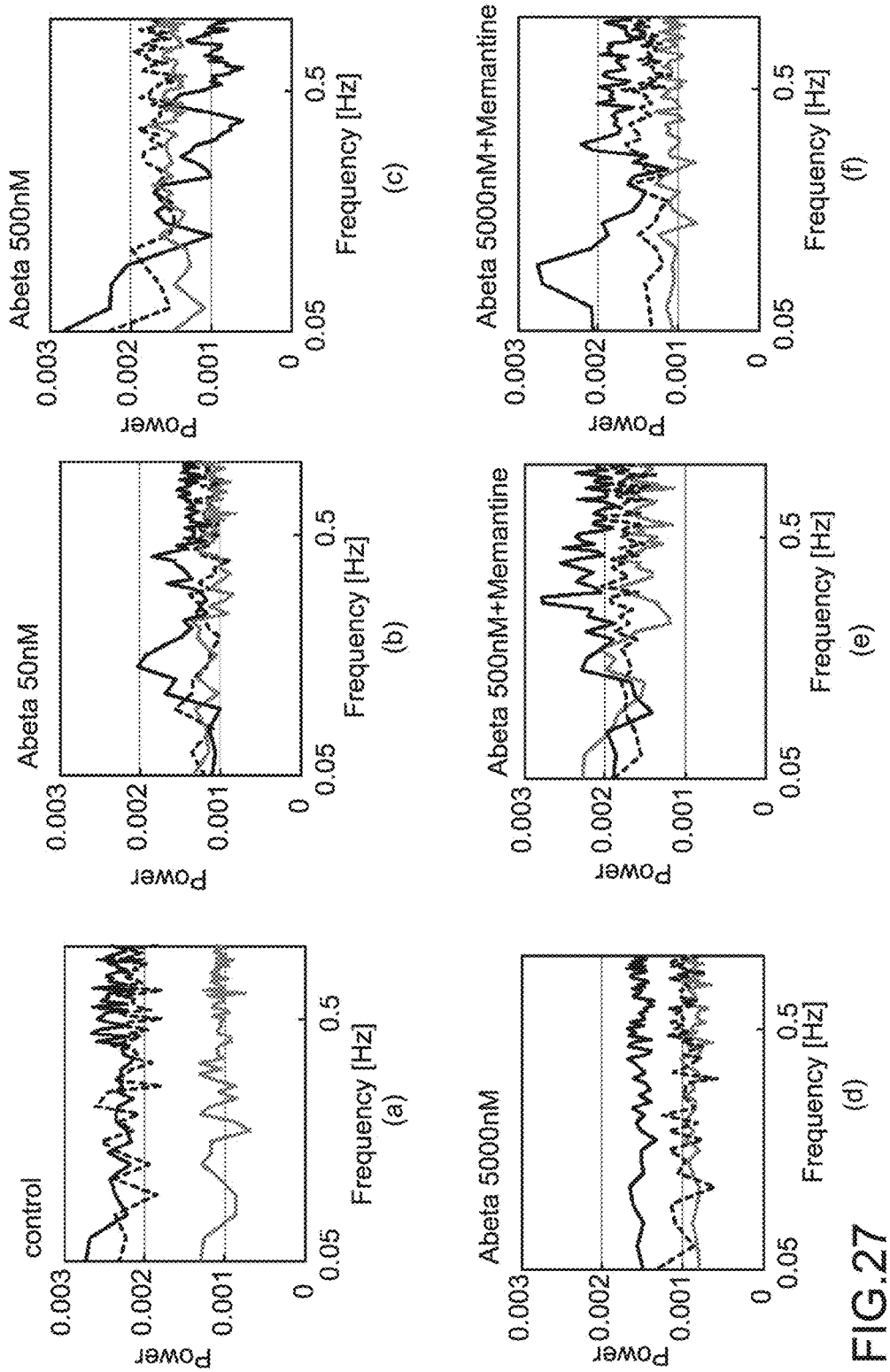
FIG. 27 Graphs of vibration characteristics of motion vibration extracted from an extraction range including a cell group to which a cytotoxic substance is administrated according to an embodiment of the present invention.

After five days, the cell image of each cell group was captured to extract the motion vibration from the whole image and each cell as the extraction range and the vibration characteristics were calculated. FIGS. 27(a) to (f) are graphs of the vibration characteristics of the motion vibration extracted from the extraction range including the whole image. FIG. 27(a) shows the vibration characteristics of the cell group to which no Aβ peptide and no memantine was administered, FIG. 27(b) shows the vibration characteristics of the cell group to which 50 nM of Aβ peptide was administered, FIG. 27(c) shows the vibration characteristics of the cell group to which 500 nM of Aβ peptide was administered, and FIG. 27(d) shows the vibration characteristics of the cell group to which 5000 nm of Aβ peptide was administered. FIG. 27(e) shows the vibration characteristics of the cell group to which 500 nM of Aβ peptide and 5 μm of memantine were administered, and FIG. 27(f) shows the vibration characteristics of the cell group to which 5000 nM of Aβ peptide and 5 μm of memantine were administered.

Figure 28:
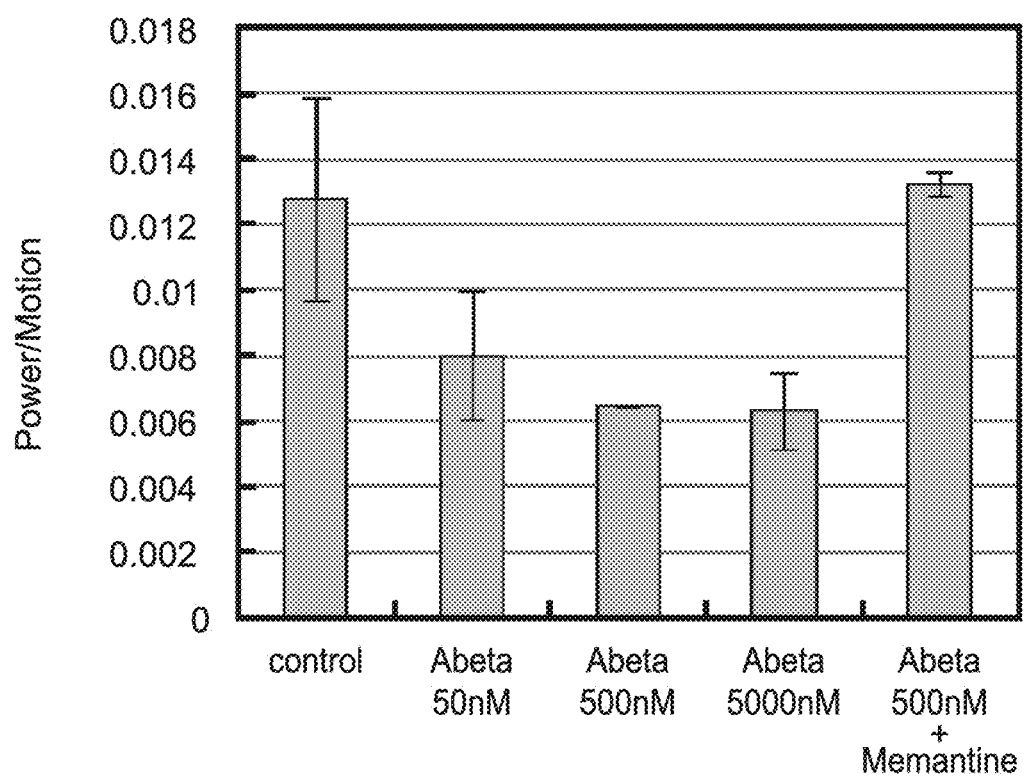
FIG. 28 A graph of vibration characteristics of motion vibration and average values of vibration magnitudes extracted from an extraction range including a cell group to which a cytotoxic substance is administrated according to an embodiment of the present invention.

FIG. 28 is a graph of average values of the vibration power extracted from the motion vibration in each cell group shown in FIGS. 27(a) to (e) in each pixel included in the extraction range. As shown in FIG. 28, as an administration amount of Aβ peptide is increased, the vibration power of the cell group is decreased. On the other hand, when memantine was administered, the vibration power is not decreased.

Figure 29:
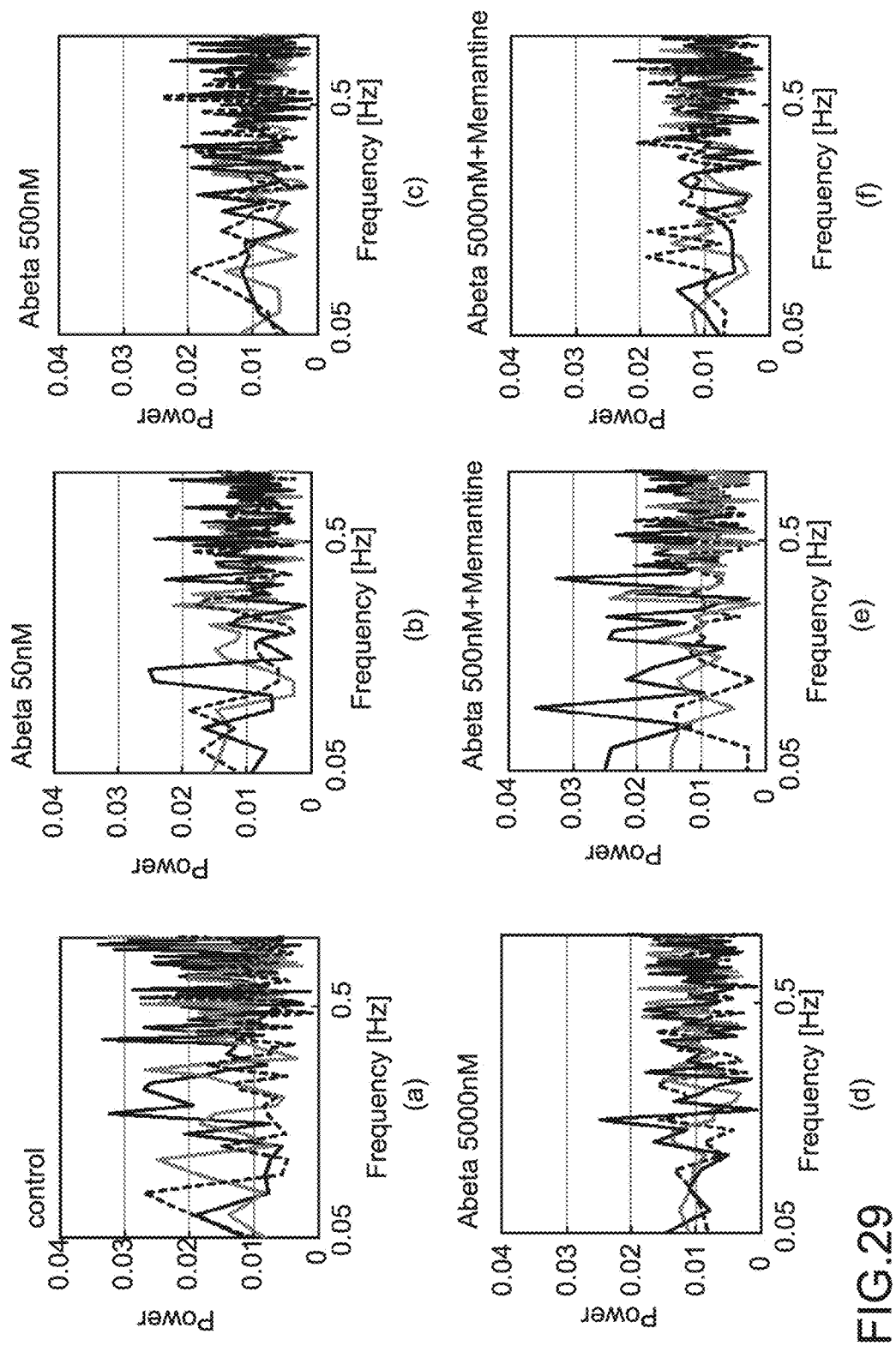
FIG. 29 Graphs of vibration characteristics of motion vibration extracted from an extraction range including individual cells to which a cytotoxic substance is administrated according to an embodiment of the present invention.

FIG. 29(a) to (f) are graphs of the vibration characteristics of the motion vibration extracted from the extraction range including the individual cells. FIG. 29(a) shows the vibration characteristics of the cell group to which no Aβ peptide and no memantine was administered, FIG. 29(b) shows the vibration characteristics of the cell group to which 50 nM of Aβ peptide was administered, FIG. 29(c) shows the vibration characteristics of the cell group to which 500 nM of Aβ peptide was administered, FIG. 29(d) shows the vibration characteristics of the cell group to which 5000 nm of Aβ peptide was administered, FIG. 29(e) shows the vibration characteristics of the cell group to which 500 nM of Aβ peptide and 5 μm of memantine were administered, and FIG. 29(f) shows the vibration characteristics of the cell group to which 5000 nM of Aβ peptide and 5 μm of memantine were administered.

Figure 30:
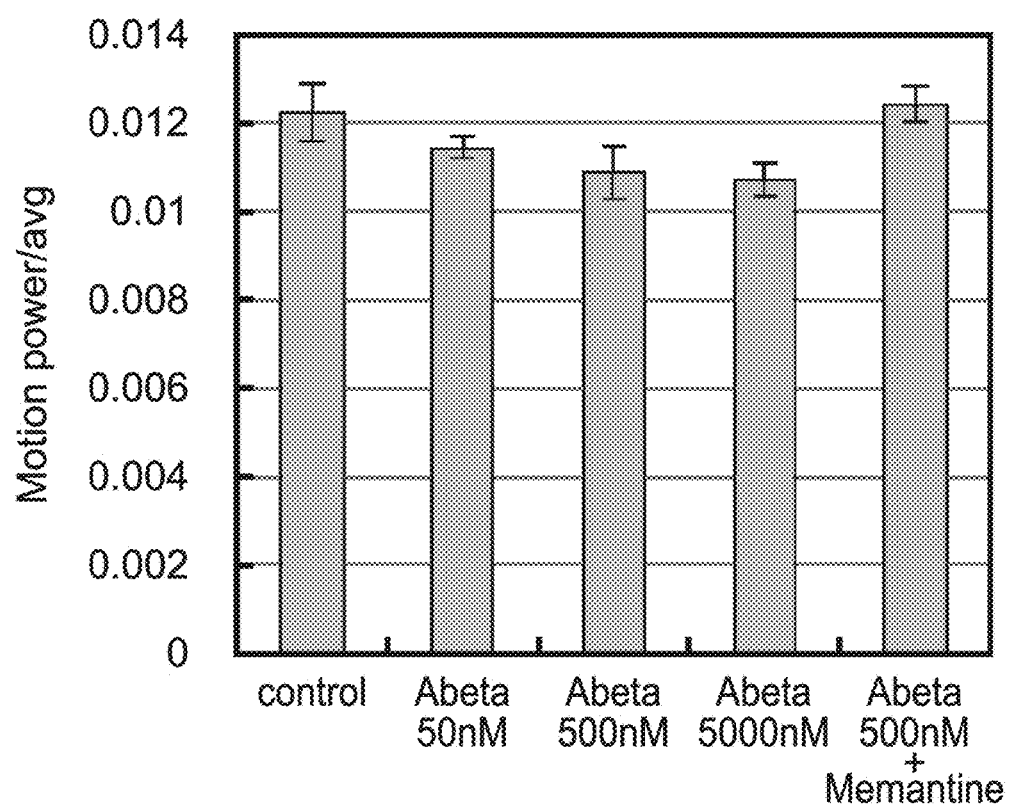
FIG. 30 A graph of vibration characteristics of motion vibration and average values of vibration magnitudes extracted from an extraction range including individual cells to which a cytotoxic substance is administrated according to an embodiment of the present invention.

FIG. 30 is a graph of average values of the vibration power extracted from the motion vibration in each cell group shown in FIGS. 29(a) to (f) in each pixel included in the extraction range. As shown in FIG. 30, although the vibration power of each cell has a tendency similar to that of the vibration power of the cell group (FIG. 25), a significant decrease of the vibration power is not recognized dissimilar to the cell group.

As described above, it is possible to evaluate the cell failure in each cell based on the vibration characteristics (FIG. 28) of the motion vibration extracted from each cell, and evaluate the neuron cell network caused by the synapse failure based on the vibration characteristics (FIG. 30) of the motion vibration extracted from the cell group.

The present technology may have the following configurations.

(1) A cell analyzer system, including:
an image acquisition unit configured to acquire a cell image by capturing a cell at elapsed time;
a vibration information extraction unit configured to extract vibration information attributable to spontaneous membrane potential vibration of a cell from the cell image;
and a vibration characteristics calculation unit configured to calculate vibration characteristics of the vibration information from the vibration information.

(2) The cell analyzer system according to (1), further including:
a range designation unit configured to designate an extraction range in the cell image, in which
the vibration information extraction unit extracts the vibration information from the extraction range.

(3) The cell analyzer system according to (1) or (2), further including:
an evaluation unit configured to evaluate one cell or a plurality of cells included in the extraction range based on the vibration characteristics.

(4) The cell analyzer system according to any one of (1) to (3), in which
the range designation unit designates a range including one cell in the cell image as the extraction range, and
the evaluation unit evaluates a type and a strength of stimulation inputted to the cell.

(5) The cell analyzer system according to any one of (1) to (4), in which
the range designation unit designates a range including a cell group including a plurality of cells as the extraction range in the cell image, and
the evaluation unit evaluates a cell network formation status in the cell group.

(6) The cell analyzer system according to any one of (1) to (5), in which
the vibration information extraction unit extracts intensity vibration of an electromagnetic wave as the vibration information.

(7) The cell analyzer system according to any one of (1) to (6), in which
the vibration information extraction unit extracts motion vibration as the vibration information.

(8) The cell analyzer system according to any one of (1) to (7), in which
the vibration characteristics calculation unit applies frequency conversion to the vibration information to calculate the vibration characteristics.

(9) The cell analyzer system according to any one of (1) to (8), in which
the vibration information extraction unit extracts a plurality types of vibration information from the extraction range.

(10) The cell analyzer system according to any one of (1) to (9), in which
the range designation unit designates a range including a cell group in the cell image and a range including a cell in the cell group as the extraction range.

(11) A cell analysis program for operating an information processing apparatus, including:
an image acquisition unit configured to acquire a cell image by capturing a cell at elapsed time;
a vibration information extraction unit configured to extract vibration information attributable to spontaneous membrane potential vibration of a cell from the cell image;
and a vibration characteristics calculation unit configured to calculate vibration characteristics of the vibration information from the vibration information.

(12) A method of analyzing a cell, including:
capturing at elapsed time a cell to generate a cell image;

extracting vibration information attributable to spontaneous membrane potential vibration of a cell from the cell image; and calculating vibration characteristics of the vibration information from the vibration information.

(13) The method of analyzing a cell according to (12), in which extracting the vibration information includes extracting the vibration information from a range including one cell in the cell image, and further including evaluating a type and an intensity of stimulation inputted to the cell based on the vibration characteristics.

(14) The method of analyzing a cell according to (12) or (13), in which extracting the vibration information includes extracting the vibration information from a range including a cell group including a plurality of cells from the cell image, and further including evaluating a cell network formation status in the cell group based on the vibration characteristics.

(15) The method of analyzing a cell according to any one of (12) to (14), in which generating the cell image includes capturing at elapsed time a plurality of cell groups separated by a flow pass that passes only cell neurites but does not pass cell bodies and incubated to generate the cell image.

100 . . . cell analysis system
101 . . . image acquisition unit
102 . . . range designation unit
103 . . . vibration information extraction unit
104 . . . vibration characteristic calculation section
105 . . . evaluation unit
106 . . . image generating unit

The invention claimed is:

1. A cell analyzer system, comprising:
circuitry configured to:
acquire a plurality of cell images by capturing a cell over an elapsed time;
determine a spontaneous membrane potential vibration of the cell, wherein:
determining the spontaneous membrane potential vibration comprises extracting, from the plurality of cell images, a variation in fluorescence intensity; and
the spontaneous membrane potential vibration indicates a change in membrane potential and the change in membrane potential indicates a change in an electrical potential of the cell membrane; and
determine a status of the cell based at least in part on the spontaneous membrane potential vibration.

2. The cell analyzer system according to claim 1, wherein extracting the variation in fluorescence intensity comprises extracting the variation in fluorescence intensity and a movement of the cell from the plurality of cell images.

3. The cell analyzer system according to claim 2, wherein the circuitry is further configured to designate an extraction range in at least one cell image of the plurality of cell images, and determine the spontaneous membrane potential vibration based on the variation in fluorescence intensity and the movement of the cell within the extraction range.

4. The cell analyzer system according to claim 3, wherein the circuitry is configured to determine the status of one cell or a plurality of cells included in the extraction range based on the variation in fluorescence intensity in the extraction range and the movement of the plurality of cells in the extraction range.

5. The cell analyzer system according to claim 4, wherein the circuitry is configured to designate, as the extraction range, a range including one cell in the cell image, and to evaluate a type and a strength of stimulation inputted to the cell.

6. The cell analyzer system according to claim 4, wherein the circuitry is configured to designate, as the extraction range, a range including a cell group including a plurality of cells, and to evaluate a cell network formation status in the cell group.

7. The cell analyzer system according to claim 1, wherein the circuitry is further configured to calculate vibration characteristics of the spontaneous membrane potential vibration.

8. The cell analyzer system according to claim 7, wherein the circuitry is configured to apply frequency conversion to the spontaneous membrane potential vibration to calculate the vibration characteristics.

9. The cell analyzer system according to claim 3, wherein the circuitry is configured to designate a range including a cell group in the cell image and a range including a cell in the cell group as the extraction range.

10. At least one non-transitory computer-readable storage medium having encoded thereon a cell analysis program that, when executed by at least one processor of an information processing apparatus, causes the information processing apparatus to carry out a method comprising:
acquiring a plurality of cell images by capturing a cell over an elapsed time;
determining a spontaneous membrane potential vibration of the cell, wherein:
determining the spontaneous membrane potential vibration comprises extracting, from the plurality of cell images, a variation in fluorescence intensity and a movement of the cell; and
the spontaneous membrane potential vibration indicates a change in membrane potential and the change in membrane potential indicates a change in an electrical potential of the cell membrane; and
determining a status of the cell based at least in part on the spontaneous membrane potential vibration.

11. A method of analyzing a cell, comprising:
capturing, over an elapsed time, a cell to generate a plurality of cell images;
determining a spontaneous membrane potential vibration of the cell, wherein:
determining the spontaneous membrane potential vibration comprises extracting, from the plurality of cell images, a variation in fluorescence intensity and a movement of the cell; and
the spontaneous membrane potential vibration indicates a change in membrane potential and the change in membrane potential indicates a change in an electrical potential of the cell membrane; and
determining a status of the cell based at least in part on the spontaneous membrane potential vibration.

12. The method of analyzing a cell according to claim 11, wherein determining the spontaneous membrane potential vibration includes determining the spontaneous membrane potential vibration from a range including one cell in at least one cell image of the plurality of cell images, and further including evaluating a type and an intensity of stimulation inputted to the cell.

13. The method of analyzing a cell according to claim 11, wherein determining the spontaneous membrane potential vibration includes determining the spontaneous membrane potential vibration from a range including a cell group including a plurality of cells from at least one cell image of the plurality of cell images, and further including evaluating a cell network formation status in the cell group.

14. The method of analyzing a cell according to claim 11, wherein generating the plurality of cell images includes capturing over an elapsed time a plurality of cell groups separated by a flow pass that passes only cell neurites but does not pass cell bodies and incubated to generate the plurality of cell images.

15. The cell analyzer system according to claim 1, wherein determining the spontaneous membrane potential vibration further comprises extracting a movement of the cell from the plurality of cell images.

* * * * *